(12) United States Patent
Osorio

(10) Patent No.: US 9,607,498 B2
(45) Date of Patent: Mar. 28, 2017

(54) METHOD, SYSTEM AND APPARATUS FOR FALL DETECTION

(71) Applicant: Ivan Osorio, Leawood, KS (US)

(72) Inventor: Ivan Osorio, Leawood, KS (US)

(73) Assignee: Ivan Osorio, Leawood, KS (US)

( * ) Notice: Subject to any disclaimer, the term of this patent is extended or adjusted under 35 U.S.C. 154(b) by 0 days.

(21) Appl. No.: 15/007,178

(22) Filed: Jan. 26, 2016

(65) Prior Publication Data
US 2016/0155312 A1 Jun. 2, 2016

Related U.S. Application Data

(63) Continuation of application No. 13/836,059, filed on Mar. 15, 2013, now abandoned.

(51) Int. Cl.
*A61B 5/00* (2006.01)
*G08B 21/04* (2006.01)
*A61B 5/0205* (2006.01)
*A61B 5/024* (2006.01)
*A61B 5/0476* (2006.01)
(Continued)

(52) U.S. Cl.
CPC .......... *G08B 21/043* (2013.01); *A61B 5/1117* (2013.01); *G08B 21/0446* (2013.01); *A61B 5/024* (2013.01); *A61B 5/0205* (2013.01); *A61B 5/0476* (2013.01); *A61B 5/0488* (2013.01);
(Continued)

(58) Field of Classification Search
CPC ....... A61B 5/013; A61B 5/117; A61B 5/1116; A61B 5/0488; A61B 2562/0219; A61B 5/1117; A61B 5/6828; A61B 5/6829; A61B 5/6831; A61B 5/112; A61B 5/113; A61B 5/1038; A61B 5/0205; A61B 5/24; A61B 5/0476; A61B 5/0816; A61B 5/1113;
(Continued)

(56) References Cited

U.S. PATENT DOCUMENTS 7,150,048 B2 * 12/2006 Buckman ............. A41D 13/018
2/455
7,558,622 B2 * 7/2009 Tran ..................... A61B 5/0022
600/509
(Continued)

OTHER PUBLICATIONS

Sposaro et al., iFall: An Android Application for Fall Monitoring and Response, 2009.*

*Primary Examiner* — Max Hindenburg
(74) *Attorney, Agent, or Firm* — Rodney J. Fuller; Booth Udall Fuller, PLC

(57) ABSTRACT

Methods, systems, and apparatuses are provided for detecting fall events of a person. Fall events are falls that are likely to occur, are occurring, or have occurred. Fall detectors and fall detector systems detect fall events of the person. Data relating to the person are received from sensors and analyzed to perform fall detection. Data relating to the person includes accelerations and forces experience by the person, changes in body position of the person, movements of the person, and body signals and sounds of the person. Neurological tests are administered to determine levels of responsiveness and awareness of the person in response to detections. Warnings are issued, and safety measures are deployed, in response to detections. Data relating to fall events are recorded and logged. Fall event histories based upon the logged data and fall detection algorithm performance are used to improve future fall detection and prediction.

20 Claims, 12 Drawing Sheets

(51) Int. Cl.
   *A61B 5/0488*    (2006.01)
   *A61B 5/08*      (2006.01)
   *A61B 5/11*      (2006.01)
   *A61B 5/1455*    (2006.01)

(52) U.S. Cl.
   CPC ......... *A61B 5/0816* (2013.01); *A61B 5/1113* (2013.01); *A61B 5/14551* (2013.01)

(58) Field of Classification Search
   CPC .. A61B 5/14551; G08B 21/02; G08B 21/043; G08B 21/0446
   See application file for complete search history.

(56) References Cited

U.S. PATENT DOCUMENTS

| | | | | |
|---|---|---|---|---|
| 8,116,724 B2* | 2/2012 | Peabody | ............. | G08B 25/016 340/539.13 |
| 8,206,325 B1* | 6/2012 | Najafi | .................. | A61B 5/1116 600/587 |
| 8,749,391 B2* | 6/2014 | Flinsenberg | .......... | A61B 5/1117 340/539.12 |
| 8,866,606 B1* | 10/2014 | Will | ........................ | H04W 4/22 340/539.11 |
| 8,868,616 B1* | 10/2014 | Otto | ................... | G06F 19/3418 378/19 |
| 8,909,497 B1* | 12/2014 | Shkolnikov | ............. | G01P 15/00 340/573.1 |
| 8,958,885 B2* | 2/2015 | Panken | ................. | A61B 5/1116 607/62 |
| 9,011,352 B2* | 4/2015 | Ten Kate | ........... | G08B 21/0446 600/595 |
| 9,138,174 B2* | 9/2015 | Jin | ....................... | A61B 5/0002 |

\* cited by examiner

METHOD, SYSTEM AND APPARATUS FOR FALL DETECTION

RELATED APPLICATION DATA

This application is a continuation of U.S. patent application Ser. No. 13/836,059, filed Mar. 15, 2013 (published as U.S. 20140276238), the content of which is incorporated by reference in its entirety for all purposes.

BACKGROUND

1. Technical Field

The subject matter described herein relates to systems and methods for anticipating and detecting falls of subjects.

2. Background Art

Falls are a grave problem for the elderly and others prone to falling. The American Council on Exercise estimates that 35%-45% of persons 65 year of age or older fall down at least once per year. Injuries, which may be serious, even fatal, are commonly associated with falling. Some current solutions for fall detection allow a person who has fallen to manually press a button for assistance. However, injuries and other effects of falls may leave a person unable to seek or obtain help. For example, a person who is unconscious or dazed and unaware of their surroundings may be incapable of utilizing existing solutions to seek help. Although falls are often regarded as accidents, the incidence of falls differs from a Poisson distribution, and this suggests causal factors are involved. The current state of the art in fall detection and aids lacks mechanisms for detecting falls and issuing warnings as falls occur or before falls occur. The current state of the art also lacks mechanisms for correlating causal factors of falls with fall detection techniques to improve the efficacy thereof.

The reporting of falls in the art is often inaccurate as people frequently have difficulty remembering details about causes of many falls. The current state of the art in fall detection and aids lacks mechanisms for tracking and reporting causal factors of falls and fall-specific data and details for treatment and prediction.

BRIEF SUMMARY

Methods, systems, and apparatuses are described for anticipating falls and detecting falls that are occurring or have occurred in subjects, substantially as shown in and/or described herein in connection with at least one of the figures, as set forth more completely in the claims.

BRIEF DESCRIPTION OF THE DRAWINGS/FIGURES

The accompanying drawings, which are incorporated herein and form a part of the specification, illustrate embodiments and, together with the description, further serve to explain the principles of the embodiments and to enable a person skilled in the pertinent art to make and use the embodiments.

Embodiments will now be described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION

1. Introduction

Figure 1A:
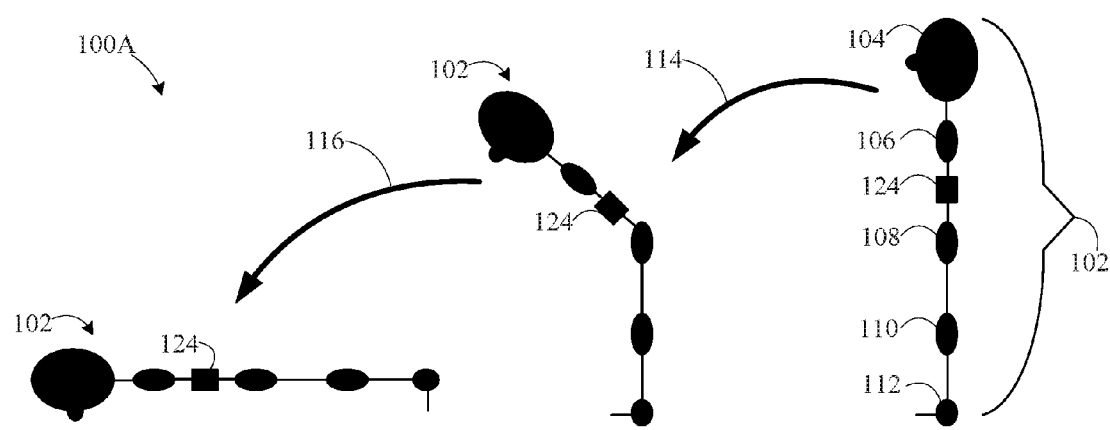
FIGS. 1A-1F are diagrams depicting types of falls that may be detected, according to exemplary embodiments.

The present specification discloses numerous example embodiments. The scope of the present patent application is not limited to the disclosed embodiments, but also encompasses combinations of the disclosed embodiments, as well as modifications to the disclosed embodiments.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Furthermore, terminology used herein to refer to a "fall" may refer to a deviation from an upright or stable position that results in an impact with an object or surface regardless of cause.

Still further, terminology used herein such as "about," "approximately," and "substantially" have equivalent meanings and may be used interchangeably.

It should be noted that the drawings described herein may not be drawn to scale unless explicitly noted.

Numerous exemplary embodiments are described as follows. It is noted that any section/subsection headings provided herein are not intended to be limiting. Embodiments are described throughout this document, and any type of embodiment may be included under any section/subsection. Furthermore, disclosed embodiments may be combined with each other in any manner.

2. Example Embodiments

The examples described herein may be adapted to various types of devices and systems for detecting falls, identifying the causative mechanism(s), determining their severity, taking actions to protect the person's body from injury, issuing warnings, and logging the information to a memory to create a history of falls for the person. Furthermore, additional structural and operational embodiments, including modifications/alterations, will become apparent to persons skilled in the relevant art(s) from the teachings herein.

In embodiments, a fall associated with a person (a "fall event") may be detected and recognized as the fall occurs, before the fall occurs, and/or after the fall occurs. Immediate and subsequent injuries and/or health problems related to falls are a serious concern to the elderly, persons with neurological disorders, persons with systemic disorders, persons with orthopedic disorders, persons with psychological disorders, and/or persons living alone, etc. Embodiments described herein provide for techniques with which early detection of falls (e.g., detection of a fall as it is occurring and/or before impact) is utilized to provide advanced warnings to persons who experience falls, safety measures as the fall is occurring, and/or assistance to persons based upon the type of fall and/or its force of impact.

Fall detection may be premised in whole or in part upon data received from fall sensors such as tri-axial accelerometers, clinometers, force transducers, gyroscopes, and/or the like. Fall detection may be premised in whole or in part upon body data and/or body signals received from the person who is falling. Additionally, warnings and neurological tests (e.g., tests of spatio-temporal orientation, reaction time tests, memory tests, and/or the like) may be administered before, during, and/or after a fall. Fall data from fall sensors as well as body data and/or body signals, responsiveness test data, and other data or information as described in the sections below may be logged and reported in embodiments.

Embodiments presented herein improve fall detection and management of the fall over the current state of the art. The embodiments presented herein may correlate past and/or current data associated with falls and/or body conditions to detect and warn of falls before, while, or after they occur. Additionally, data related to falls may be logged and reported to improve fall detection efficacy and fall treatment.

For instance, methods, systems, and apparatuses are provided for detecting a person who is falling or has fallen. In an example aspect, a method is disclosed. The example method is for detecting a fall. The method includes receiving data from at least one sensor associated with a person, and analyzing the received data to detect changes therein. The method also includes detecting the person is falling or that a fall is imminent based on the analysis of the received data and issuing a warning. The method further includes administering to the person, in response to the detection, a neurological test requiring the person to manually or orally input a level of responsiveness or awareness. Still further, the method includes logging to a memory at least of one a date and time of the fall or one or more results of a test administered to the person.

In another example aspect, a method is disclosed. The example method is for detecting whether a person has fallen. The method includes receiving a measure of force from a sensor associated with the person, and analyzing the measure of force with respect to time. The method also includes detecting the person has fallen based on the analysis of the measure of force with respect to time. The method further includes administering to the person, in response to the detection, a neurological test requiring the person to manually or orally input a level of responsiveness. Still further, the method includes logging to a memory at least one of, the date and time of the fall, the force of impact or the results of the neurological test, and issuing a warning in response to the detection that the person has fallen.

In yet another example aspect a fall detection system is disclosed. The fall detection system includes at least one sensor associated with a user, and a fall detection unit coupled to the at least one sensor and configured to filter and analyze a measure of force determined by the at least one sensor and determine at least one of the user falling, the user has fallen, or a fall of the user is imminent. The fall detection system also includes a neurological unit coupled to the fall detection unit and configured to administer a neurological test to the user in response to the at least one of the user falling, the user having fallen, or a fall of the user being imminent. The fall detection system further includes a user-input unit coupled to the neurological unit and configured to receive a neurological test input from the user. Still further, the fall detection unit includes a communication unit coupled to the fall detection unit and to the neurological unit, and configured to communicate with at least one of a care-giver station, an emergency medical technology station, or a remote entity.

In a further example aspect, a fall detection system is disclosed. The fall detection system includes at least one of a tri-axial accelerometer, a clinometer, a force transducer, or a gyroscope attached to a user. The fall detection system also includes a fall detection unit coupled to the at least one of the tri-axial accelerometer, the clinometer, the force transducer, or the gyroscope, and configured to filter and analyze motion data received from the at least one of the tri-axial accelerometer, the clinometer, the force transducer, or the gyroscope and determine if the user is falling or that a fall is imminent. The fall detection system further includes a neurological unit coupled to the fall detection unit and configured to administer a responsiveness test to the user and a user-input unit coupled to the neurological unit and configured to receive a responsiveness test input from the user.

Various example embodiments are described in the following subsections. In particular, example falls that may be detected in embodiments are described, followed by example fall factors and effects. Fall detector embodiments are subsequently described including embodiments that determine fall causes and that manage situations associated with falls. This is followed by a description of further example advantages and embodiments for fall detection. Next, example operational embodiments are described. Finally, an example computer-implemented embodiment is described.

3. Example Falls

Falls may occur in various ways that depend on factors such as, but without limitation, the body position of a person, movements or activities of the person, the neurological, autonomic, and/or psychological state(s) of the person, environmental conditions, and/or the like. The force of impact and severity of the fall may depend on such factors, as will be discussed below in this section. In the context of FIGS. 1A-1F, as described herein, a fall of a person is depicted. As shown, person 102 may have a fall detector 124 attached to, or associated with, their body.

For example, FIG. 1A shows person 102 experiencing fall 100A. Person 102, as depicted, has body pivot points that may affect fall type and impact. That is, person 102 includes a head 104, a neck 106, a waist 108, a knee joint (knee joints) 110, and an ankle joint (ankle joints) 112. Each of these body joints or pivot points, alone or in any combination, may allow for various body positions before, during, and after fall 100A. Fall 100A of FIG. 1A includes two parts: an initial fall portion 114 and a final fall portion 116.

It should be noted that person 102, as described above with respect to FIG. 1A, is reproduced in FIGS. 1A-1H. Head 104, neck 106, waist 108, knee joint (knee joints) 110, and ankle joint (ankle joints) 112 are shown in FIGS. 1B-1H without their reference numeral designators only for clarity of illustration. Reproductions of person 102 are designated as person 102, but each reproduction instance includes head 104, neck 106, waist 108, knee joint (knee joints) 110, and ankle joint (ankle joints) 112.

Fall 100A of FIG. 1A may begin with person 102 in an upright, standing position. As a result of initial fall portion 114 (in a forward direction), person 102 is in an intermediate position such that person 102 is bending at waist 108. From this intermediate position, person 102 may continue fall 100A through final fall portion 116. The result of final fall portion 116 is person 102 lying face-down and prone (e.g., substantially flat) on the floor or ground. In fall 100A as shown, person 102 may experience injuries such as facial/skull trauma with fractures, brain trauma, neck trauma (e.g., cervical spine injuries), broken/fractured bones (e.g., shoulder(s), collarbone(s), and arm(s)), and/or the like. Initial fall portion 114 brings person 102 closer to the ground relative to the standing position from which fall 100A began. Due to this intermediate body position, person 102 may experience less severe impact and/or injury as a result of fall 100A than as a result of the fall depicted in FIG. 1E below, for example.

Figure 1B:
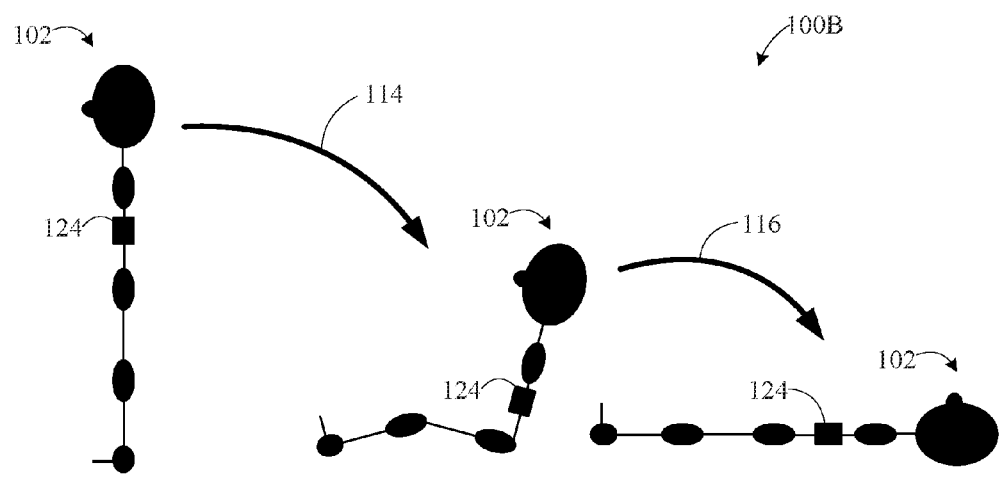

FIG. 1B shows another example of person 102 experiencing fall 100B. Person 102, again as depicted, has body pivot points that may affect fall type and impact. That is, person 102 includes head 104, neck 106, waist 108, knee joint (knee joints) 110, and ankle joint (ankle joints) 112 as described above. Each of these body pivot points, alone or in combination, may allow for various body positions before, during, and after fall 100B. Fall 100B of FIG. 1B includes two parts: initial fall portion 114 and final fall portion 116.

Fall 100B of FIG. 1B may begin with person 102 in an upright, standing position. As a result of initial fall portion 114 (in a backward direction), person 102 is in an intermediate position such that person 102 is bending at waist 108 and knee joint 110 with the person's buttocks (i.e., a body part proximate waist 108) having impacted the floor/ground. From this intermediate position, person 102 may continue fall 100B through final fall portion 116. The result of final fall portion 116 is person 102 lying face-up and prone (e.g., substantially flat) on the floor or ground. In fall 100B as shown, person 102 may experience injuries such as skull fractures, brain injuries, neck trauma/cervical spine damage, broken/fractured bones (e.g., hip(s) and arm(s)), and/or the like. Initial fall portion 114 brings person 102 closer to the ground relative to the standing position from which fall 100B began. Due to this intermediate body position, person 102 may experience less impact and/or injury as a result of fall 100B than that associated with FIG. 1E depicted below, for example. It is possible, however, that greater injury to head 104 and/or neck 106 may occur due to a whiplash effect caused by the transition from the intermediate position to the final position via final fall portion 116.

Figure 1C:
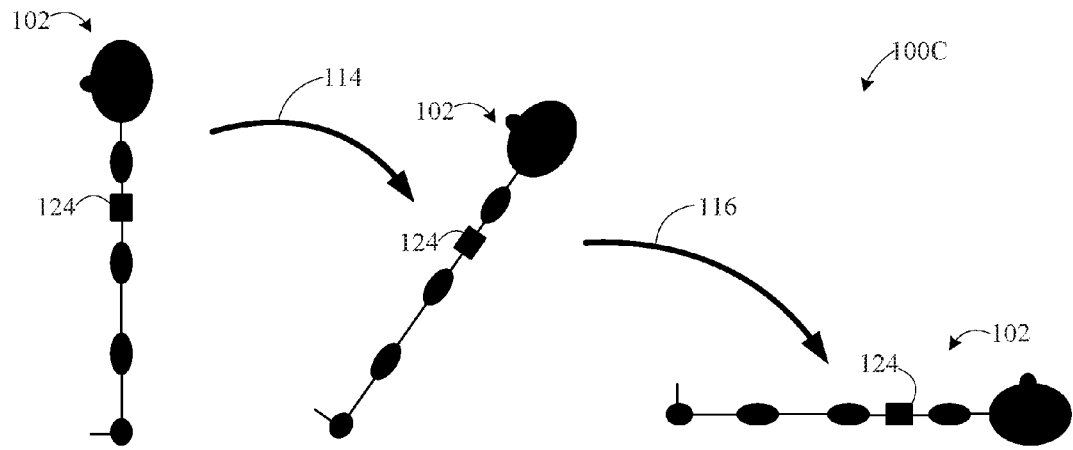

FIG. 1C shows yet another example of person 102 experiencing fall 100C. Person 102, again as depicted, has body pivot points that may affect fall type and impact. That is, person 102 includes head 104, neck 106, waist 108, knee joint (knee joints) 110, and ankle joint (ankle joints) 112 as described above. Each of these body pivot points, alone or in combination, may allow for various body positions before, during, and after fall 100C. Fall 100C of FIG. 1C includes two parts: initial fall portion 114 and final fall portion 116.

Fall 100C of FIG. 1C may begin with person 102 in an upright, standing position. As a result of initial fall portion 114 (in a backward direction), person 102 is in an intermediate position such that person 102 is not bending at any pivot points (e.g., the body of the person is stiff) or has a substantially linear body plane. From this intermediate position, person 102 continues fall 100C through final fall portion 116. The result of final fall portion 116 is person 102 lying face-up and prone (e.g., substantially flat) on the floor or ground. In fall 100C as shown, person 102 may experience injuries such as skull fractures, brain injuries, neck trauma/cervical spine cord injuries, broken/fractured bones (e.g., hip(s) and arm(s)), and/or the like. As shown, fall 100C brings person 102 to the ground from the standing position from which fall 100C began without pause or interruption of motion. Due to this this type of fall, person 102 may experience greater injury to head 104 and/or neck 106 due to the unmitigated impact of the transition (fall 100C) from the initial position to the final position.

Figure 1D:
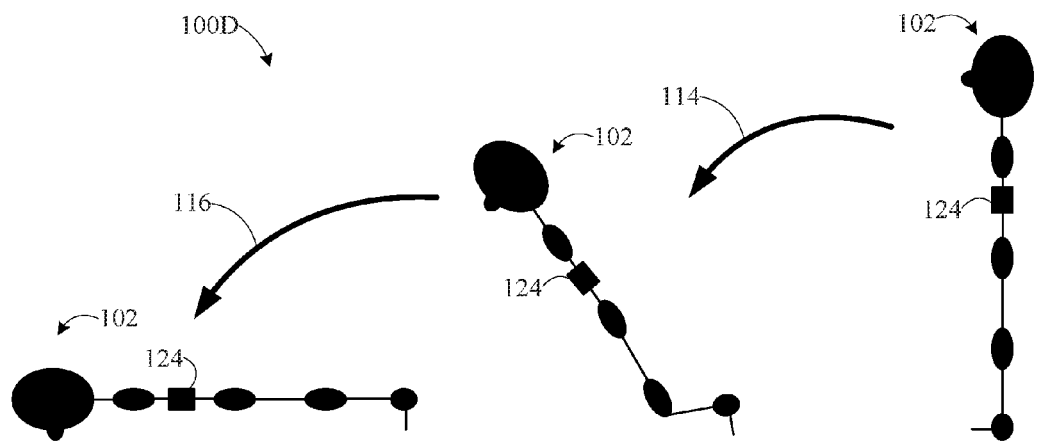
Figure 1E:
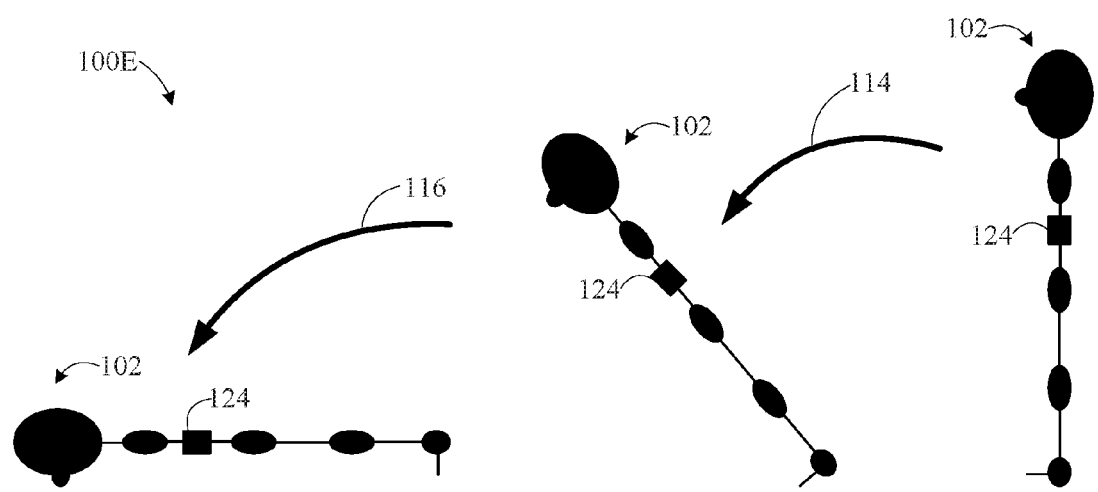

FIG. 1D shows still yet another example of person 102 experiencing fall 100D. Person 102, again as depicted, has body pivot points that may affect fall type and impact. That is, person 102 includes head 104, neck 106, waist 108, knee joint (knee joints) 110, and ankle joint (ankle joints) 112 as described above. Each of these body pivot points, alone or in combination, may allow for various body positions before, during, and after fall 100D. Fall 100D of FIG. 1D includes two parts: an initial fall portion 114 and a final fall portion 116.

Fall 100D of FIG. 1D may begin with person 102 in an upright, standing position. As a result of initial fall portion 114 (in a forward direction), person 102 is in an intermediate position such that person 102 is bending at knee joint 110 with knee joint 110 having impacted the floor/ground. From this intermediate position, person 102 may continue fall 100D through final fall portion 116. The result of final fall portion 116 is person 102 lying face-down and prone (e.g., substantially flat) on the floor or ground. In fall 100D as shown, person 102 may experience injuries such as facial/skull trauma, neck trauma, knee injury, broken/fractured bones (e.g., shoulder(s), collarbone(s), and arm(s)), and/or the like. In this example fall, initial fall portion 114 brings person 102 closer to the ground relative to the standing position from which fall 100D began. Due to this intermediate body position, person 102 may experience less severe impact and/or injury to head 104 and/or neck 106 as a result of fall 100D.

FIG. 1E shows a further example of person 102 experiencing fall 100E. Person 102, again as depicted, has body pivot points that may affect fall type and impact. That is, person 102 includes head 104, neck 106, waist 108, knee joint (knee joints) 110, and ankle joint (ankle joints) 112 as described above. Each of these body pivot points, alone or in combination, may allow for various body positions before, during, and after fall 100E. Fall 100E of FIG. 1E includes two parts: an initial fall portion 114 and a final fall portion 116.

Fall 100E of FIG. 1E may begin with person 102 in an upright, standing position. As a result of initial fall portion 114 (in a forward direction), person 102 is in an intermediate position such that person 102 is not bending at any pivot points (e.g., person's body is stiff) or has a substantially linear body plane. From this intermediate position, person 102 may continue fall 100E through final fall portion 116.

The result of final fall portion 116 is person 102 lying face-down and prone (e.g., substantially flat) on the floor or ground. In fall 100E as shown, person 102 may experience injuries such as facial/skull trauma, brain damage, neck trauma/spinal cord damage, broken/fractured bones (e.g., shoulder(s), collarbone(s), and arm(s)), and/or the like. As shown, fall 100E brings person 102 to the ground from the standing position from which fall 100E began without pause or interruption of motion. Due to this this type of fall, person 102 may experience greater injury to head 104 and/or neck 106 due to the unmitigated impact of the transition (fall 100E) from the initial position to the final position.

Figure 1F:
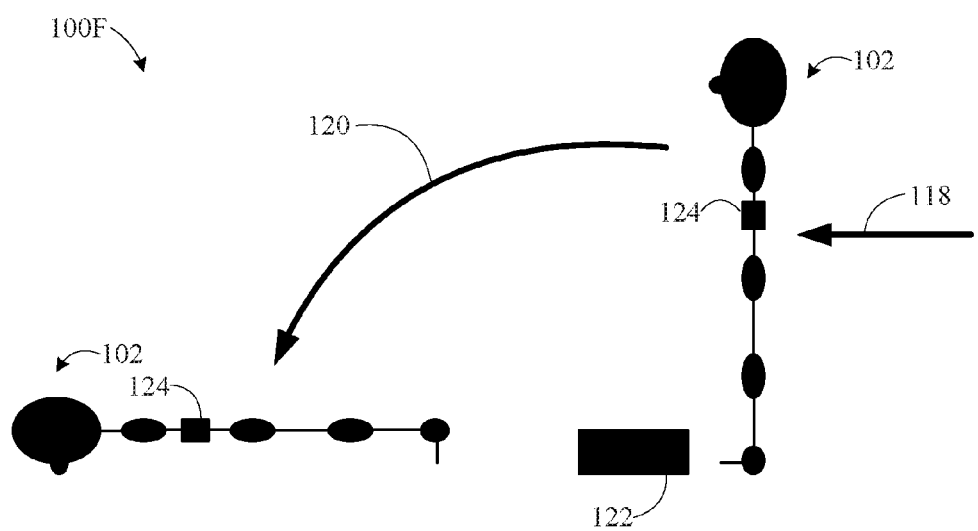

FIG. 1F shows yet a further example of person 102 experiencing fall 100F. Person 102, again as depicted, has body pivot points that may affect fall type and impact. That is, person 102 includes head 104, neck 106, waist 108, knee joint (knee joints) 110, and ankle joint (ankle joints) 112 as described above. Each of these body pivot points, alone or in combination, may allow for various body positions before, during, and after fall 100F. Fall 100F of FIG. 1F includes two parts: an initial movement 118 and a fall portion 120.

Fall 100F of FIG. 1F may begin with person 102 in an upright, standing position. As a result of initial movement 118 (shown as a forward movement), person 102 may trip or stumble over obstruction 122 (e.g., at or around ankle joint 112 or knee joint 110). Person 102 then falls via fall portion 120. The result of fall portion 120 is person 102 lying face-down and prone (e.g., substantially flat) on the floor or ground. In fall 100F as shown, person 102 may experience injuries such as facial/skull trauma, neck trauma, broken/fractured bones (e.g., shoulder(s), collarbone(s), and arm(s)), and/or the like. Initial movement 118 may increase the velocity that person 102 experiences during fall 100F. Due to initial movement 118, person 102 may experience more severe impact and/or injury as a result of fall 100F. Additionally, as shown, fall 100F brings person 102 to the ground from the standing position from which fall 100F began without pause or interruption of motion which may also result in more severe injuries. It is also contemplated that fall 100F of FIG. 1F may, in exemplary falls similar to fall 100F, be caused by a force applied to person 102 at any part of the body (e.g., a push or object that collides with person 102) such that a velocity or movement is applied to person 102 before fall portion 120 begins. It is further contemplated that a person may collide with a stationary object at any part of the body incurring a force upon the body and that such a force may result in a fall.

While FIG. 1F is shown with initial movement 118 in a forward direction, it is contemplated that an initial backward movement into an obstruction may cause fall 100F with the resulting fall 100F being similar to that described above with respect to FIG. 1B (fall 100B) or FIG. 1C (fall 100C), in examples. Likewise, fall portion 120 may be a two-stage fall similar to fall 100F described above with respect to FIG. 1D (fall 100D), in examples. Also, while not depicted, falls caused by slippery surfaces (e.g., ice, spilled liquids, etc.) are also contemplated in example falls described in this disclosure.

It is further contemplated that the example falls described with respect to FIGS. 1A-1F are not exhaustive, or exclusive with respect to each other, and that other types of falls, as well as falls which are combinations of the described falls 100A-100F are considered to be within the scope of the description provided herein as would be apparent to a person of skill in the relevant art(s) having the benefit of this disclosure. For example, initial positions of person 102 may include sitting in a chair, standing on a ladder, and/or the like. Similarly, falls 100A-100F may occur to the left or right sides of person 102 in addition to forward and backward, or may occur in combinations of directions (e.g., backward and to the left). Further, person 102 may fall and land in a seated position or on their hands and knees, or person 102 may break or attempt to break their fall using arm movements, all of which may affect the force of impact and outcome of a given fall. Still further, the position of the body of person 102 immediately after the fall may be based upon the fall type, such as those described with respect to FIGS. 1A-1F (e.g., falls 100A-100F). It should be appreciated that the techniques described herein are equally applicable to various fall type examples.

It should also be noted that, while not shown for the sake of brevity, multi-axial falls may occur such that fall direction along a given axis may change during the fall due to autonomic and/or environmental factors such as muscle tone (e.g., a person becoming tense or stiff as they fall), body movements (e.g., a person attempting to break or prevent their fall such as with arm movements), objects or obstructions in the path of the fall (e.g., a person coming in contact with furniture during the fall), and/or the like.

Exemplary fall factors and effects are described next.

4. Example Fall Factors and Effects

A. Example Fall Factors

As noted in the above-described examples of falls 100A-100F in FIGS. 1A-1F respectively, a person may experience many different types of falls. Similarly, many different factors relating to falls may be used to detect, predict, mitigate, protect from, treat, and warn of falls. For example, but without limitation, the body position of a person, movements or activities of the person, the neurological, autonomic, nutritional, fitness level and/or psychological status of the person, environmental conditions, and/or the like, may contribute to a fall and/or the type of fall experienced by a person. Exemplary fall factors are discussed in further detail below in this section.

For instance, autonomic factors may be associated with falls and fall types. One such autonomic factor classification is cardiovascular factors. Cardiovascular factors may include deviation in heart rate and decreased blood flow to the brain resulting in syncope. Decreased blood flow to the brain may also result in loss of awareness, loss of balance or a person swaying, loss of postural tone (e.g., in anti-gravitatory muscles or their respective antagonists), loss of vision, loss of coordination and/or motor skills, etc., and if severe enough, decreased blood flow may result in loss of consciousness. Even minor loss of blood flow may result in transient vision loss or impairment which can result in a person swaying, stumbling or deviating in gait, or tripping. Muscle weakness and/or low glucose levels are also factors associated with falls.

Muscle tone is another fall factor. Increases or decreases in muscle tone above or below critical levels (e.g., thresholds) measured, for example, with electromyography (EMG), may result in falls and determine how a person falls. Increases in muscle tone indicate an increased force of contraction of a muscle, and decreases in muscle tone indicate a decreased force of contraction (i.e., a relaxing) of a muscle. For example, increased muscle tone during a fall may result in a the body being more rigid and thus a greater risk of head injury is present because of the body position during fall (e.g., as described above with respect to FIGS. 1C and 1E). Increased or decreased muscle tone may also cause a person to fall in a certain direction. For example, decreased tone in muscles such as the quadriceps may cause a person to fall in a forward direction, with the knees being the first body part to hit the ground. In contrast, increased tone in muscles such as the paraspinal muscles, hamstrings or one or more of the gluteal group may in essence "pull" a person into a fall in the backward direction. It should be noted that deviations in muscle tone (e.g., with respect to quadriceps, hamstrings, gluteal group muscles, etc.) on the left or right side of the body may also cause a fall to the left or right side of the person.

Further, factors such as muscle tone and heart rate may provide an indication that a fall is imminent. For instance, onset of bradycardia or tachycardia in conjunction with loss of muscle tone or sway may indicate a fall is likely or about to occur.

Figure 1G:
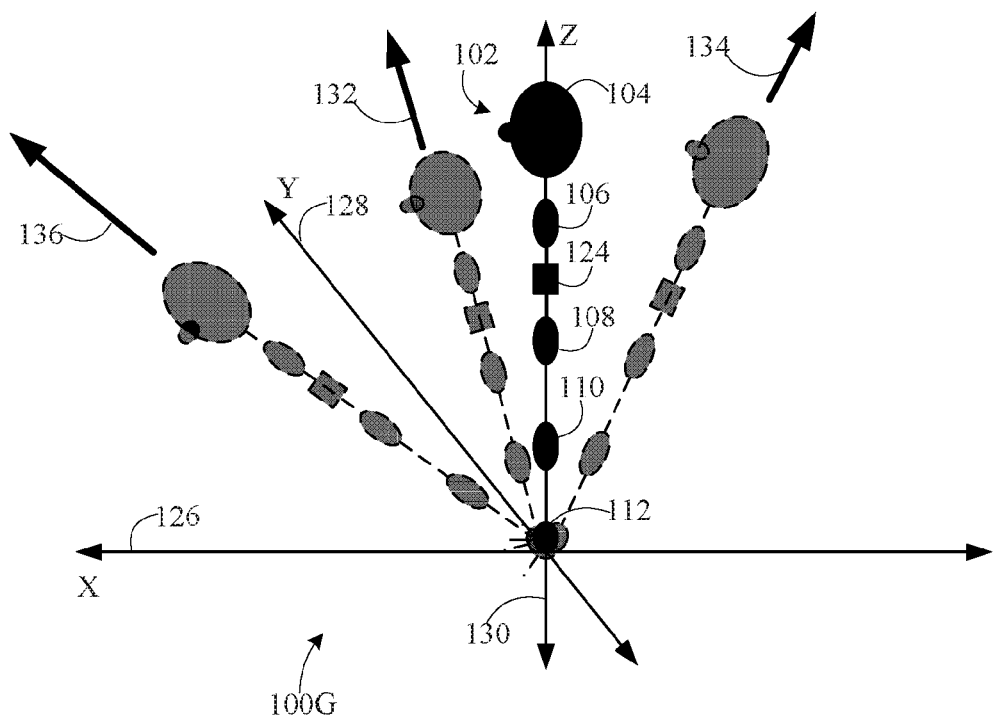
FIGS. 1G-1H are diagrams depicting deviations in body position that may be detected, according to exemplary embodiments.

For instance, exemplary deviations in body position 100G of person 102 are illustrated in FIG. 1G. Person 102, again as depicted, has body pivot points that may affect fall type and impact. That is, person 102 includes head 104, neck 106, waist 108, knee joint (knee joints) 110, and ankle joint (ankle joints) 112 as described above. As shown, person 102 may have a fall detector 124 attached to, or associated with, their body, and may be oriented in space relative to an X-axis 126, a Y-axis 128, and a Z-axis 130. Exemplary clinometer outputs (e.g., from a clinometer as described herein) showing deviations (e.g., vectors with angle and rate of change components) from the vertical or erect posture of a person (as depicted along Z-axis 130) are also depicted. Deviations leading to falls (depending on the magnitude of the angle and its rate of change) may result in falls to the ground. For example, a deviation 132 is indicative of sideways or lateral deviations that may lead to a fall in a lateral direction (as shown, to the person's right side along Y-axis 128), a deviation 134 is indicative of a backward deviation that may lead to a fall in the backward direction (as shown, behind the person along X-axis 126), and a deviation 136 is indicative of a forward deviation that may lead to a fall in the forward direction (as shown, in front of the person along X-axis 126).

Figure 1H:
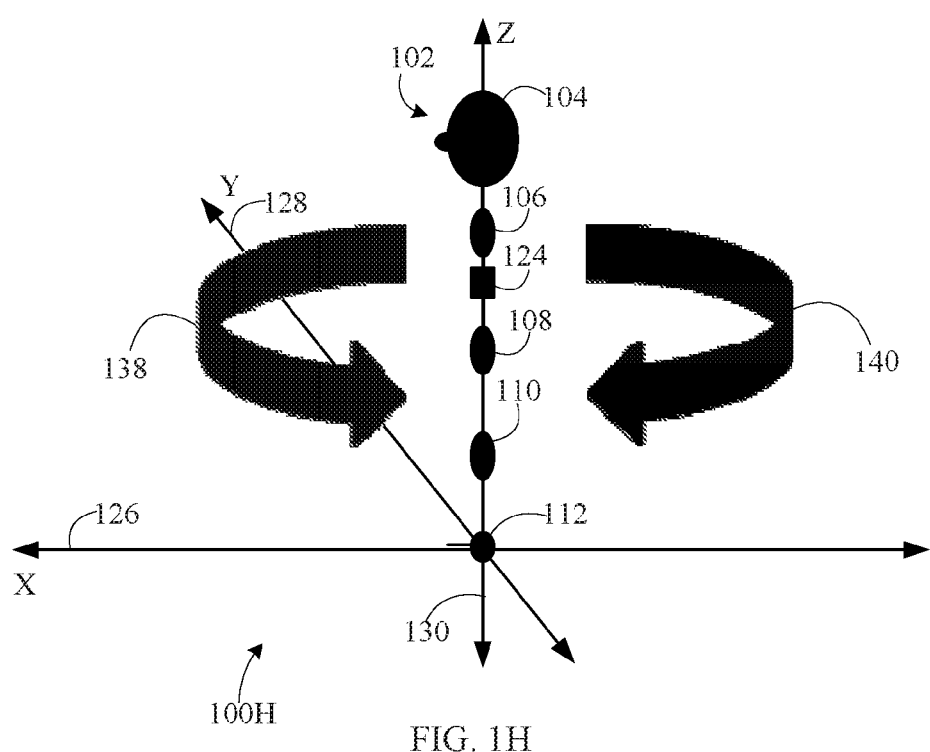

Other exemplary deviations in body position 100H of person 102 are illustrated in FIG. 1H. Person 102, again as depicted, has body pivot points that may affect fall type and impact. That is, person 102 includes head 104, neck 106, waist 108, knee joint (knee joints) 110, and ankle joint (ankle joints) 112 as described above. As shown, person 102 may have a fall detector 124 attached to, or associated with, their body, and may be oriented in space relative to an X-axis 126, a Y-axis 128, and a Z-axis 130. Deviations in body position 100H exemplify illustrations of a person's sway (although other types of sway and body jerks not shown are also contemplated herein) that may be detected by sensors such as, but not limited to, a clinometer, a gyroscope, or tri-axial accelerometer. For example, a sensor may detect a deviation 138 that indicates person 102 is rotating from right to left about their upright, standing axis (e.g., Z-axis 130, as shown), or may detect a deviation 140 that indicates person 102 is rotating from left to right about their upright, standing axis (e.g., Z-axis 130, as shown).

Swaying may be a precursor to falling and may have predictive/anticipatory value for falls. Decreases or increases in the tone of anti-gravitatory muscles or a change in a ratio of tone/force between agonists and antagonists muscles may also occur before an actual fall (e.g., a fall to the ground as depicted in FIGS. 1A-1F described above). Use of EMG or of force detectors/transducers placed on muscles controlling posture may allow early prediction or detection (e.g., before the person hits the ground or before downward falling movement) of falls. For instance, fall detections may be based upon detected EMG data indicating abnormally high muscle tone or abnormally decreased muscle tone (e.g., in one or more anti-gravitatory muscles or one or more of their respective antagonists). Recoding of brain waves (e.g., electroencephalography (EEG)) may also be used to predict or detect falls. With respect to EEG, a rapid transition from a waking background (e.g., 8-13 Hz for a normal adult) or of low amplitude high frequency rhythms (e.g., >13 Hz) to: a) diffuse flattening, b) bilateral or unilateral high voltage delta (e.g., 0.1-3.9 Hz), or c) sudden emergence of sleep rhythms in a person not in a recumbent position are associated with a high probability of falling to the ground. Additionally, epileptiform activity originating from certain brain regions, with a certain duration, amplitude, and/or extent of spread is highly temporally correlated with falls to the ground.

Other fall factors include directly neurological factors. These factors may be classified as central factors or peripheral factors. For instance, central factors may include decreased brain function due to seizures (e.g., epilepsy). Other central factors include strokes (both past and present) and movement disorders such as Parkinson's disease which may also result in motor dysfunction and incoordination. Brain tumors, syncope, and vestibule-cerebellar dysfunction (e.g., dizziness (including effects of intoxicants) or clumsiness) are also factors that make a person prone to falling.

Neurological factors classified as peripheral factors include muscle diseases (dystrophies), peripheral neuropathies (e.g., damage to peripheral nerve as is common in diabetics), as well as brain and spinal diseases/lesions, such as multiple sclerosis (MS), which may also result in sensory, motor, or other forms of dysfunction.

Still other factors include bone and joint diseases, as well as substance abuse (e.g., alcohol and drugs) which may impair the normal body state, capabilities or movement of a person.

Still further, environmental factors may be associated with falls and fall types. For instance, obstructions in walkways, surface conditions (e.g., slippery surfaces or changes in surfaces), steps or stairs, obstacles to movement such as entering a bathtub or shower, inclines or declines, visual obstructions, difficult to reach items, and distractions may be environmental factors. Additionally, time of day (or night) may be an environmental factor due to fatigue and/or impaired vision due to lack of light or sensitivity due to brightness of light.

One or more of the above fall factors may be used in determining that a fall is occurring or has occurred, as described in sections below, and may be used to provide a warning(s), mitigation, treatment(s), and/or the like to a person. For instance, fall factors associated with the body (e.g., autonomic, neurological, etc.) may have corresponding body signals and/or movements which may be monitored (e.g., electrocardiography (EKG), electroencephalography (EEG), blood oxygen saturation, eye movement monitoring (presence of nystagmus indicating vestibule-cerebellar dysfunction), balance or coordination, etc.) and may be used for estimation of risks of fall and determination of fall mechanisms or causes.

B. Example Fall Effects

Different types of falls and/or their associated factors may lead to various fall effects, according to embodiments. In some cases, the combination of a fall with fall factor symptoms, as described in the preceding subsection, may result in increased severity of overall fall effects.

For example, as noted in the preceding sections, injuries are commonly associated with falls. Fall effects include physical injuries such as broken and/or fractured bones, torn ligaments, dislocated joints, bruises, lacerations, puncture wounds, brain and spinal cord injuries such as concussions or contusions, and/or the like. Physical injuries may be sustained at different parts of the body depending on the type of fall and the force of impact. Psychological injuries may also manifest in a person who experiences one or more falls. For instance, fall effects also include lack of confidence or self-esteem, hesitancy, lack of socialization and activities due to mental or physical state, and/or the like. The above-mentioned injuries may lead to decreased freedom/ability of movement or faculties of a person who has fallen. Such conditions may be temporary or permanent, and may lead to additional falls.

Another fall effect of interest is the "lie time" which may be the amount of time (e.g., a time interval) a person spends lying prone on the ground or floor after a fall. In embodiments, the duration of the lie time may be linked to fall severity and overall effect of a fall on a person at the time immediately after the fall as well as days, weeks, months, or even years after the fall. Longer lie time durations increase morbidity with respect to fall related issues.

According to embodiments, fall effects also include decreased responsiveness and decreased awareness and/or cognitive function. Responsiveness indications may be reflex/automatic motor or verbal (e.g., formed or unformed vocalizations) responses of which a person is not aware. In contrast, indications of awareness and cognitive function may include a person knowing or understanding their actions and later having memory of them.

For example, a person may be unconscious after a fall. Thus the person is neither responsive nor aware/functioning cognitively (i.e., abnormal responsiveness level, abnormal awareness level and abnormal cognitive function level). Similarly, a person may be conscious but unresponsive, unaware of their surroundings or condition and unable to perform tasks such as standing up, calling/yelling for help, complaining of pain and/or the like. A person may be aware that they have fallen and may have a substantially normal level of responsiveness (i.e., be able to perform rudimentary tasks such as calling/yelling for help, complaining of pain, etc.), but the person may be unable to reason or perform more complex tasks such as operating a phone or an electronic device. Put another way, some responsiveness on the part of a person may not be determinative of a requisite level of awareness or cognitive function, or of a lack of impairment. For example, in such a state, a person may have a normal or substantially normal level of responsiveness, but an abnormal level of awareness and/or cognitive function. Further, a person who has sustained minimal effects from a fall may have normal or approximately normal levels of responsiveness, awareness, and cognitive function. Still further, a person may have normal responsiveness, awareness, and cognitive levels, but may be unable to move or stand due to physical injury sustained (e.g., broken/fractured bones, dislocated joints, sprains, spinal cord injury, and/or the like) or magnified by a fall. Each of these described conditions may require a specific response (e.g., warning, treatment, mitigation, information, communication, and/or the like) that may be administered to a person after a fall has been detected, as described in further detail in the next section.

Vital signs (also referred to as a subset of body data and/or body signals) may also be affected by a fall. Heart rate, respiratory rate, respiratory tidal volume, blood oxygen saturation, EEG, and EKG are exemplary vital signs, according to embodiments. Vital signs that are abnormal, that exceed or fall below threshold values, and/or that deviate from baseline values may indicate fall severity and/or the overall effect of a fall on a person.

The next section describes exemplary fall detector embodiments.

5. Example Fall Detector Embodiments

A. Fall Detector Device and System

Figure 2:
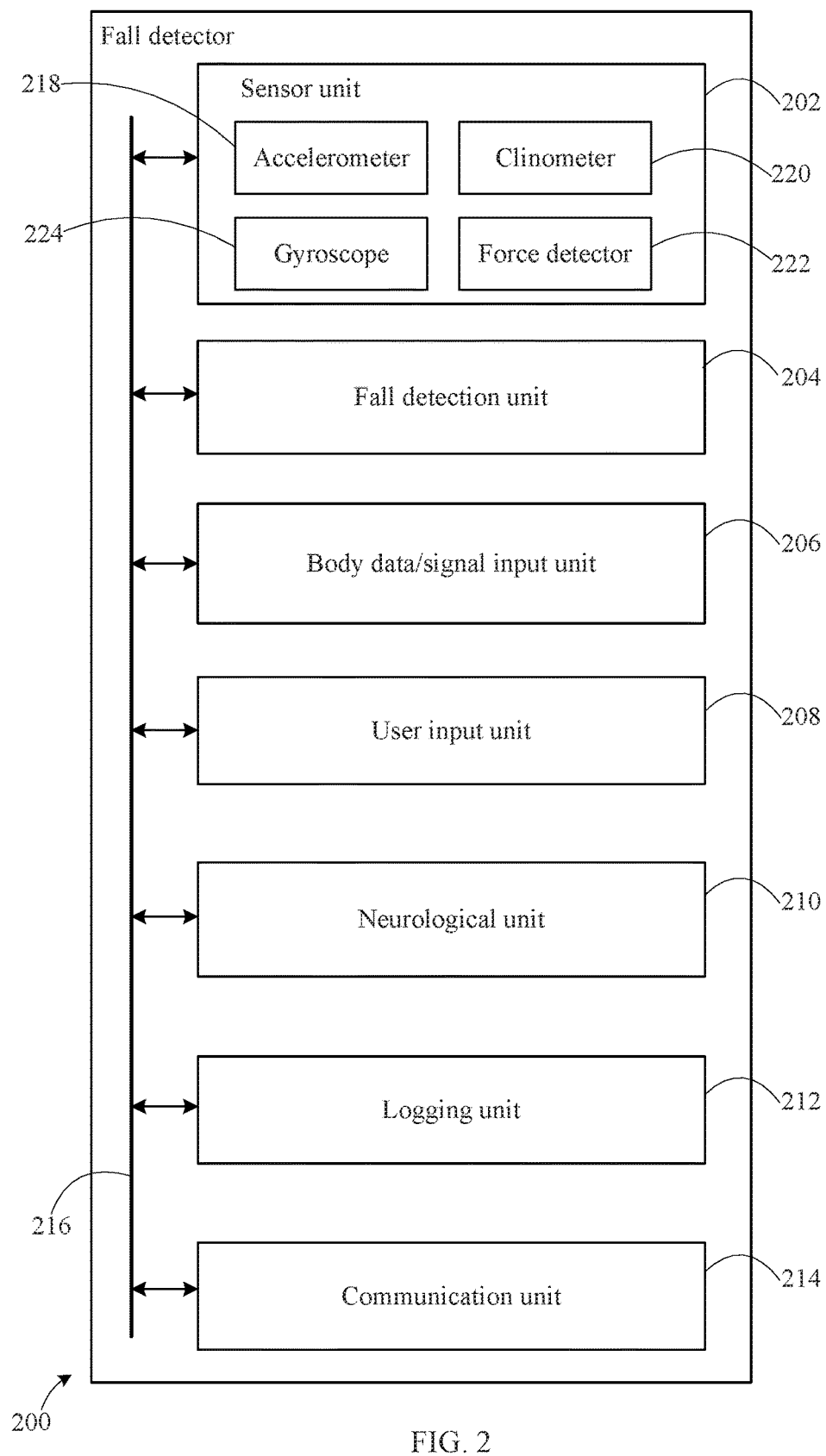
FIG. 2 is a block diagram of a portion of a fall detecting system, according to an exemplary embodiment.

Predicting or detecting falls may be performed in various ways, according to embodiments. For example, according to embodiments, falls are detected and/or confirmed as they occur and before fall impact. In other embodiments, falls are detected and/or confirmed after the impact of the fall is sustained by a person. To detect falls in accordance with the embodiments described herein, and exemplary fall detector will now be described. A fall detector may be configured in various ways to perform fall detection. For instance, FIG. 2 shows a portion of an exemplary fall detector 200, in accordance with an embodiment.

Fall detector 200 includes various components and sub-components. As shown, fall detector 200 includes a sensor unit 202, a fall detection unit 204, a body data/signal input unit 206, a user input unit 208, a neurological unit 210, a logging unit 212, and a communication unit 214. Each of these units may transmit information or data to, and receive information or data from, one or more other units via communication link 216. Communication link 216 may use any wired or wireless communication protocol to communicate information or data. It should be appreciated that the exchange of information or data as shown in FIG. 2 is exemplary and that other connections between the depicted units may be used in embodiments.

Sensor unit 202 includes the following components in the depicted embodiment: an accelerometer 218, a clinometer 220, a force detector 222 (a force transducer), and a gyroscope 224. In some embodiments, any or all of these sensors may be included. For example, embodiments may contain only one of accelerometer 218, clinometer 220, force detector 222, or gyroscope 224, or any combination thereof. While not shown, it is contemplated that sensor unit 202 may also include a global positioning system (GPS) component. Each component of sensor unit 202 is configured to determine and/or collect motion data associated with a person. Motion data may include movement of a person as well as lack of movement, body position during movement, and any parameters associated with movement such as velocity, acceleration or changes thereof, impact force, and/or the like, according to embodiments.

Accelerometer 218 may be a tri-axial accelerometer that measures acceleration and/or changes in acceleration along one or more of three axes. In embodiments, accelerometer 218 may be a micro electro-mechanical systems (MEMS) accelerometer. Clinometer 220 may measure the degree of incline of the body with respect to a reference incline. In embodiments, clinometer 220 may include one or more inclinometer components and/or one or more declinometer components. Force detector 222 may measure "high-G" impacts, for example, at the conclusion of a fall when a person impacts the ground/floor. Such high-G impacts may be caused by abrupt changes in acceleration due to impacts (e.g., high negative accelerations at impacts and/or rebound accelerations immediately after impacts). In embodiments, force detector 222 may comprise one or more force transducers. Gyroscope 224 may measure deviations in balance (e.g., deviations from an upright position) such as sway, stumbling, and/or deviations in gait. In embodiments, sensor unit 202 is configured to receive and/or determine sensor data indicating that a person may fall, is falling, or has fallen using sensor data from one or more of accelerometer 218, clinometer 220, force detector 222, and/or gyroscope 224. For example, sensor data indicating acceleration on two axes (e.g., forward and downward) coupled with a body incline deviating from an upright reference value just prior to the acceleration may be provided to fall detection unit 204 to determine a person is falling. Similarly, if a person sways or stumbles, sensor data related to the swaying may be provided to fall detection unit 204 to determine that a fall is imminent and deploy safety/mitigation measures (as in further detail discussed below).

Fall detection unit 204 is configured to detect and verify that a person is falling or has fallen based upon data and/or information received from one or more other components of fall detector 200. Such data and/or information may be provided as input to a fall detection algorithm. For instance, in the above example, sensor data indicating an acceleration on one or more axes (e.g., two axes: forward and downward) coupled with a body incline or body sway deviating from an upright reference value just prior to the acceleration as determined by sensor unit 202 may be provided to fall detection unit 204. Fall detection unit 204 may determine that a fall is occurring based upon a detection of force with respect to a time interval or based upon combination of force and incline prior thereto. Fall detection unit 204 may determine that a fall is occurring based upon a combination of motion-related data (e.g., acceleration) and temporally correlated body data signal or fall factor such as, but without limitation, fall factors described in Section 4.A, Example Fall Factors. As such, fall detection unit 204 is also configured to verify that a fall is occurring or has occurred.

Fall detection unit 204 is also configured to determine that a fall is likely or imminent based on a fall detection algorithm. A detection of an imminent fall may be based on one or more of motion-related data (e.g., acceleration), body incline (see FIG. 1G), body sway (see FIG. 1H), any fall factors described herein such as, but without limitation, fall factors described in Section 4.A, Example Fall Factors, and/or a fall history of a person, such as a history based on logged fall events maintained by logging unit 212 described in further detail below. Changes in body signals with predictive values may also be utilized to detect imminent falls. For instance, if a person is being monitored for EMG signals related to muscles such as the quadriceps, an elevated signal value may indicate that the person is standing, and if an elevated value is followed by a sudden involuntary drop (e.g., a lack of any other bodily movement of a person may indicate an involuntary drop as could be determined via sensor unit 202) there exists a high probability of an imminent fall. In other examples, vertigo, detected by an onset of nystagmus, indicates a probability of an imminent fall, and arrhythmia or a sudden drop in heart rate (e.g., a decrease in instantaneous heart rate of 50 beats per minute) may also be predictive. Changes in body signals with predictive values may also be utilized in conjunction with a fall history to provide more definitive detections of imminent falls.

Figure 7:
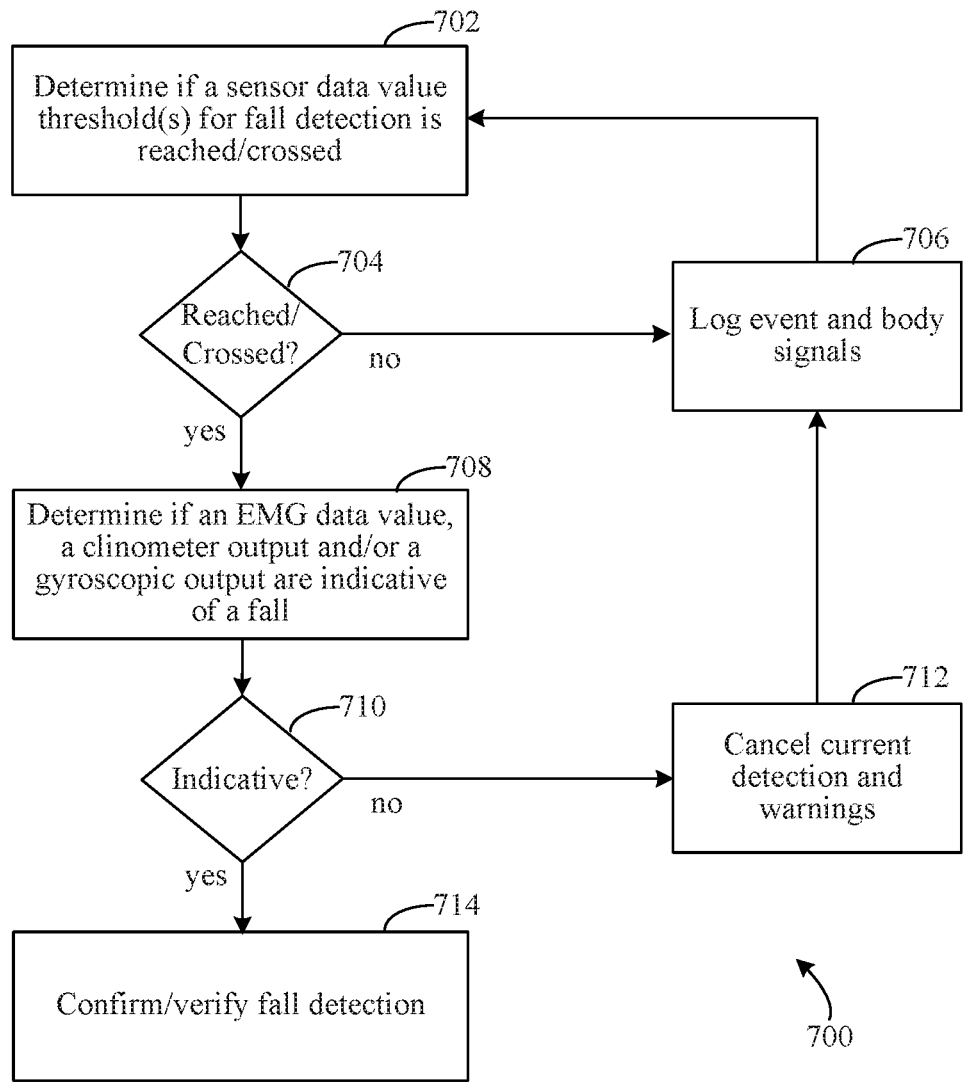
FIG. 7 is a flowchart providing example steps for a fall detection algorithm, according to an exemplary embodiment.

Exemplary fall detection algorithm details are further discussed below with respect to FIGS. 7 and 8.

Fall detection unit 204 is also configured to issue warnings related to falls. In embodiments, the issuance of warnings includes notifying the person, family or acquaintances of the person, care givers, medical practitioners, and remote entities such as a 911 service. Warnings may be provided from fall detection unit 204 via user input 208 and/or communication unit 214. Warnings may be upgraded or downgraded based on a value of the force of impact of the fall. For example, fall detection unit 204 may cause the warning to be upgraded or downgraded based upon data received from sensor unit 202, such as from accelerometer 218 and/or force detector 222. In embodiments, falls for which the value of the force of impact is above a threshold value may have upgraded warnings as described herein, whereas falls for which the value of the force of impact is below a threshold value may have downgraded warnings as described herein. Warnings may also be upgraded or downgraded based upon body data, body signals, and/or vital signs before, during and/or after a fall.

Further, in example embodiments, fall detection unit may deploy and/or administer, or cause to be deployed and/or administered (e.g., by issuing commands or the like), various safety measures as described herein. In some embodiments, fall detection unit 204 (or fall detector 200) may include a safety measures unit or a body protection unit (not shown) configured to perform the deployment and/or administration of the safety measures. Safety measures and/or their respective components may be housed within fall detection unit 204 (or fall detector 200), the safety measures unit and/or the body protection unit. In other embodiments, safety measures and/or their respective components may be housed outside fall detector 200, but may still be operatively/communicatively coupled to fall detector 200 (i.e., as a fall detection system).

Fall detection unit 204 is also configured to categorize types of falls, categorize possible causes of falls, and rank fall severity. Types of falls (e.g., such as those described in Section 3, Example Fall Embodiments and FIGS. 1A-1F) may be determined and/or categorized based on motion data associated with a fall (e.g., from components in sensor unit 202) and/or from fall impact locations. In some embodiments, data/signals from force or impact detectors placed at various locations on the body of a person may be used to determine one or more points of impact on the body of the person.

Causes of falls may be determined based, wholly or in part, on one or more of the following factors: a type of fall, a presence or absence of breaking arm movements, a body part that first makes contact with a surface, a body position before the fall, a body position during the fall, a direction of the fall, a body position immediately after the fall, a type of kinetic activity before the fall, an amount of time elapsed since the last kinetic activity of the person, a type and/or a level of kinetic activity, autonomic activity after the fall, or neurologic activity after the fall. These factors may be determined by fall detection unit 204, or may be determined by other components of fall detector 200, as described herein, and received by fall detection unit 204 via communication link 216.

The severity of a fall may be ranked according to a number of factors such as, but not limited to, vital signs associated with a fall, a force of fall impact, a level of pain associated with a fall, the lie time after a fall, injuries caused or exacerbated by a fall, the locations of such injuries, an activity of the person at the time of a fall, a location of the person, and/or any other factors or effects described herein, as would become apparent to one of skill in the relevant art(s) having the benefit of this disclosure. In embodiments, fall detection unit 204 may sum a severity score linked to various fall factors and fall effects, as well as other indicia of fall severity described herein, to determine an overall fall severity ranking. In other embodiments, the number of fall factors, fall effects, and/or the like may be determinative of the fall severity ranking. In other embodiments, different techniques may be utilized to determine fall severity rankings as would become apparent to a person of skill in the relevant art(s) having the benefit of this disclosure.

Body data/signal input unit 206 is configured to receive body data and/or body signals from a person. For example, heart rate, electric or electromagnetic activity of the body, certain body movements or ocular activity such as nystagmus, and/or the like, may be received. While not shown, as would become apparent to a person of skill in the relevant art(s) having the benefit of this disclosure, body sensors such as, but not limited to, EMG, EEG, EKG, visual/optical/photic, force and/or other types of sensors placed on or proximate to the body of a person and attached to fall detector 200 via interfaces/connections may provide the body data and/or body signals. In some embodiments, data/signals from force or impact detectors placed at various locations on the body of a person may be used to determine one or more points of impact on the body of the person.

User input unit 208 is configured to receive inputs from a user/person. User input unit 208 may include an audio input interface, a touch screen interface, one or more buttons, a display interface, and/or other user input components. The user inputs may be provided in response to prompts (visual, audio, haptic, etc.), questions, puzzles and/or games presented to the person by neurological unit 210, for example. Inputs may be in the form of pressing one or more buttons on fall detector 200, manipulating a touch screen with finger swipes, speaking or making other vocal indications, shaking or moving fall detector 200, or providing any such inputs via a remote device linked to fall detector 200 via communication unit 214. In embodiments, a person may say their location as an input to user input unit 208, and the location of the person may be used to obtain and/or dispatch assistance. In embodiments, components of user input unit 208, such as a touch screen and a display interface may also be used to provide tests, information, and/or prompts from user input unit 208, fall detection unit 204, neurological unit 210, logging unit 212, and/or communication unit 214 to a person experiencing a fall event.

Neurological unit 210 is configured to determine and/or test levels of responsiveness, awareness, and cognitive function of a person who has fallen. In embodiments, such testing may be referred to as neurological testing and may include responsiveness tests, awareness tests, and/or cognitive function tests. Such tests may include orientation tests (with one or more questions selected from topics including the person's history, personal identification, current events, temporal setting, spatio-temporal orientation, and current physical environment), motor function tests (e.g., reaction time tests), and memory tests. For example, when a fall has been verified by fall detection unit 204, neurological unit 210 may prompt the user to indicate a level of responsiveness, awareness, and/or cognitive function by soliciting a response from the person in the form of neurological tests such as one or more of prompts (visual, audio, haptic, noxious stimuli, etc.), questions, puzzles and/or games. In some embodiments, a responsiveness test is administered first, and upon passing the responsiveness test, an awareness or cognitive function test may be subsequently administered. If a person fails the responsiveness test (e.g., the person has an abnormal level of responsiveness), the same test or other responsiveness tests may be re-administered/administered before proceeding to an awareness or cognitive test. Similarly, if a person fails an awareness test or a cognitive test, the same test or other awareness/cognitive tests may be administered/re-administered.

In embodiments, awareness tests and/or cognitive tests may be re-administered based on at least one of motor activity of the person (e.g., based on EMG, output(s) of a sensor(s) of sensor unit 202, etc.), one or more sounds associated with the person (e.g., respiratory sounds, speech and/or vocalizations), and/or a time interval (e.g., the duration of lie time or the amount of time since the last neurological test). For example, a person experiencing convulsions or seizures, or a person lying motionless may be indications that an awareness/cognitive test should be re-administered. Similarly, a person groaning, screaming, crying, or yelling, or a person not speaking may also be indications that an awareness/cognitive test should be re-administered. Further, an increase in lie time or an amount of time a person has been attempting to rise from a fall may be indications that an awareness/cognitive test should be re-administered.

Neurological unit 210 may prompt a person to type, vocalize, or select from a list of options, the cause of a fall. A person may also be prompted to describe or select a level of pain or a level of severity associated with the fall.

Neurological unit 210 may operate in conjunction with user input unit 208 and/or communication unit 214 to administer tests and/or prompts to a person.

Logging unit 212 is configured to log data or information associated with a fall (e.g., acceleration, body incline, impact force, body data/signals, responsiveness data, time spent lying on the ground, information about how the person got off the ground, and/or the like). Data or information associated with a fall may be received by logging unit 212 from one or more components of fall detector 200 via communication link 216. Logging unit 212 may include one or more storage devices (described in further detail below in the Example Computer Embodiments section with respect to example computer 900) in which data or information associated with a fall may be stored.

Logging unit 212 may also be configured to perform reporting functions in which data or information received from the components of fall detector 200 and/or stored in logging unit 212 may be reported to the person that is falling or has fallen or to a remote entity such as a care giver, a care giver station, a medical practitioner, an emergency responder, a family member of the person, etc. Such reports may also be stored in logging unit 212 and may be transmitted from fall detector 200 to an external device in a wireless or wired manner. Reports may be used by a person or a medical practitioner to diagnose, treat, and/or predict falls by assessing risk factors and conditions that may cause falls (e.g., by establishing patterns linked to temporal factors and intervals of falls, body signal/body state precursors, etc.). For example, a person who experiences a fall is more likely to fall again and this effect is compounded by increasing numbers of falls. Thus, prediction, mitigation, and/or prevention of any number of falls is very beneficial.

Communication unit 214 is configured to communicate data and information determined and/or collected by fall detector 200 to remote devices such as handheld devices, computers and computing devices, smart phones, and or the like. Communication unit 214 is also configured to receive data and information from such remote devices. The exchange of data and information with remote devices may be performed by communication unit 214 via wired and/or wireless transfer. Communication unit 214 may also receive software/firmware upgrades associated with fall detector 200 that may include new or modified definitions of thresholds and reference values, new or modified detection algorithms, and/or the like.

It is also contemplated that one or more of each of accelerometer 218, clinometer 220, force detector 222, and/or gyroscope 224 may be included in fall detector 200 and/or sensor unit 202.

While not shown, fall detector 200 may include one or more attachment components configured to affix/attach fall detector 200 to a person. For example, clamps, clips, adhesives, ties, bands, latches and/or the like may be used to attach fall detector 200 (or any component thereof) to a person or their clothing. Additionally, different locations for placement of a fall detector such as fall detector 200 (or any component thereof) on the body of a person may be utilized, along with a determined fall type, to determine which part of the body sustained the greatest impact and/or injury as a result of a fall. Thus, in embodiments, more than one fall detector (e.g., fall detector 200 (or any component thereof)) may be used, independently or in conjunction, by a person concurrently. Further, fall detector 200 and/or any of its components described herein, may include a clock or timer that may be used in the embodiments as described in this disclosure.

Fall detector 200 and each of the components/elements included therein may be implemented in hardware, or a combination of hardware and software and/or firmware. Fall detector 200 and each of the components included therein may include functionality and connectivity beyond what is shown in FIG. 2, as would be apparent to persons skilled in relevant art(s). However, such additional functionality is not shown in FIG. 2 for the sake of brevity.

B. Example Safety Measures

As noted above, embodiments described herein provide for mitigation of the effects due to the force of impact of a fall. For example, upon detection that a fall is occurring or is imminent, safety measures such as inflatable devices and/or shock absorbing devices may be deployed. Inflatable devices may include vests (chest, torso, and/or lower back protection), neck supports, head protection, hip protection, knee joint(s) protection and/or the like and may be activated when a fall is detected to cushion fall impact.

Other exemplary safety measures may include audio instructions that inform a person of the likelihood of severe injury based upon the type of fall, location of impact, and/or force of impact. Such instructions may inform the person to remain still even though the person may have normal responsiveness, awareness, and cognitive function levels. In such cases, help may be automatically notified by the fall detector (e.g., fall detector 200) allowing the person to avoid exacerbation of injuries.

Additional safety measure embodiments include providing visual, audio, haptic, electrical, thermal and/or noxious stimuli to increase the level of awareness of a person. For example, low voltage electrical contacts, cold contacts, loud noises, bright displays, vibrations, smelling salts, and/or the like may be administered to bring the person to a requisite level of responsiveness, awareness, or cognitive function such that person may seek help.

In the case of precursors of falls (such as body swaying, stumbling, deviations in gait, and/or other changes in body posture or joint position, changes in heart rate, blood pressure and/or the like), the person may be instructed to not stand up, or, if already standing up, to sit down, or to lie down to prevent the fall. For persons with impaired vision or impaired sensation in their limbs or extremities, and/or factors that make them prone to falling, a camera with ground recognition capabilities may be coupled to or associated with the person to help the person navigate safely. For example, when approaching obstacles and/or irregular or slippery ground, the camera, via the fall detection unit (e.g., fall detection unit 204), may issue a warning or instruct the patient via an audio and/or visual command to stop moving and/or take a different route.

According to embodiments, safety measures and devices, as well as stimuli, may be deployed and/or administered by fall detection unit 204. In some embodiments, safety measures and devices, as well as stimuli, may reside as separate units on the body of a person or apart from a person, but are still considered to be part of a fall detection device/system and/or fall detection unit 204.

Further example embodiments and advantages are described in the next section.

6. Further Example Embodiments and Advantages for Fall Detection

The embodiments described herein enable the detection of falls. The fall detection techniques of the described embodiments allow for detection of falls before, during, and after they occur. By detecting a falls that are imminent and that are occurring, safety measures may be utilized to reduced injuries and other effects of falls. Fall detection may be adapted and improved (e.g., reducing or eliminating false positives and providing more accurate detection of real falls) by adapting the techniques used in fall detection algorithms based on fall histories of persons and performance of the algorithms. As described herein, falls may be detected based upon motion data, force data, body signals and/or body data, predictive patterns of falls, fall factors, or any combination thereof. This allows for flexible and robust early fall detection which in turn provides opportunities to mitigate fall effects.

It will be recognized that the systems, their respective components, and/or the techniques described herein may be implemented in hardware, software, firmware, or any combination thereof, and/or may be implemented as hardware logic/electrical circuitry. The disclosed technologies can be put into practice using software, firmware, and/or hardware implementations other than those described herein. Any software, firmware, and hardware implementations suitable for performing the functions described herein can be used, such as those described in the following sections.

7. Example Operational Embodiments

Figure 3:
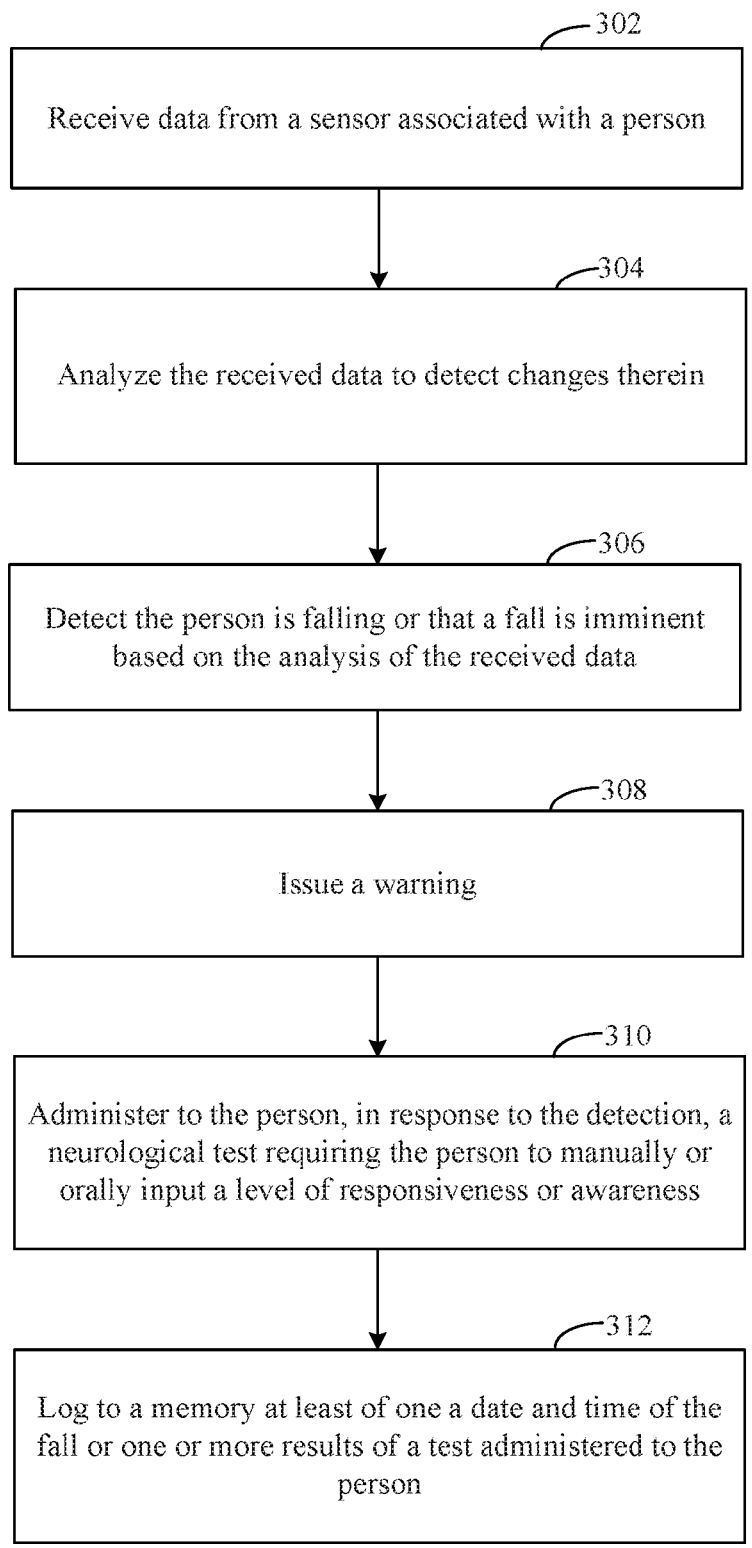
FIG. 3 is a flowchart providing example steps for performing fall detection, according to an exemplary embodiment.

The embodiments described herein may perform their functions in various ways. For example, FIG. 3 shows a flowchart 300 providing example steps for detecting a fall, according to an exemplary embodiment. Fall detector 200 of FIG. 2 and computer 900 of FIG. 9 (described below) may each operate according to flowchart 300, in embodiments. Other structural and operational embodiments will be apparent to persons skilled in the relevant art(s) based on the discussion regarding flowchart 300. Flowchart 300 is described as follows.

Flowchart 300 may begin with step 302. In step 302, data from a sensor associated with a person may be received. The sensor may be one or more components of sensor unit 202 of FIG. 2, and the data may be received by fall detection unit 204. For example, accelerometer 218 may transmit data related to acceleration along one or more of up to three axes, and the data may be received at fall detection unit 204. In embodiments, data from clinometer 220, force detector 222, and/or gyroscope 224 may be received. In other embodiments, body data/signals may be received from other sensors or monitoring components as described herein.

In step 304, the received data may be analyzed to detect changes therein. For example, changes in acceleration along at least one axis of tri-axial accelerometer 218 may be analyzed by fall detection unit 204 in accordance with embodiments described herein. Other received data as described in step 302 may also be analyzed.

In step 306, it may be detected that the person is falling or that a fall is imminent based on the analysis of the received data. The fall detection may be done in accordance with the description of fall detection unit 204 set forth in Section 5.A above, or in accordance with flowchart 700 of FIG. 7, and fall detection may also be done in accordance with FIG. 8.

In step 308, a warning may be issued. For example, fall detection unit 204 may issue the warning. In embodiments, the warning may be any type of warning described herein and may be issued to the person with whom the fall is associated, a care giver, family member, medical practitioner, remote entity (e.g., emergency responders), and/or the like.

In step 310, a neurological test requiring the person to manually or orally input a level of responsiveness or awareness may be administered to the person, in response to the detection in step 306. Neurological tests may be administered by neurological unit 210 as described above.

In step 312, at least one of a date and time of the fall or at least one result of a test administered to the person may be logged to a memory or a storage device. For example, logging unit 212 may log the results, information and data in a memory such as a memory within fall detector 200, within logging unit 212, and/or within computer 900 as described below.

It is also contemplated that, while flowchart 300 is described in terms of receiving data from a sensor, one or more accelerometers (e.g., accelerometer 218), clinometers (e.g., clinometer 220), force detectors or transducers (e.g., force detector 222), and/or gyroscopes (e.g., gyroscope 224) may be used in embodiments.

In some example embodiments, one or more steps 302, 304, 306, 308, 310, and/or 312 of flowchart 300 may not be performed. Moreover, steps in addition to or in lieu of steps 302, 304, 306, 308, 310, and/or 312 may be performed. Further, in some example embodiments, one or more of steps 302, 304, 306, 308, 310, and/or 312 may be performed out of order, in an alternate sequence, or partially (or completely) concurrently with other steps.

Further operational embodiments are discussed next.

Figure 4:
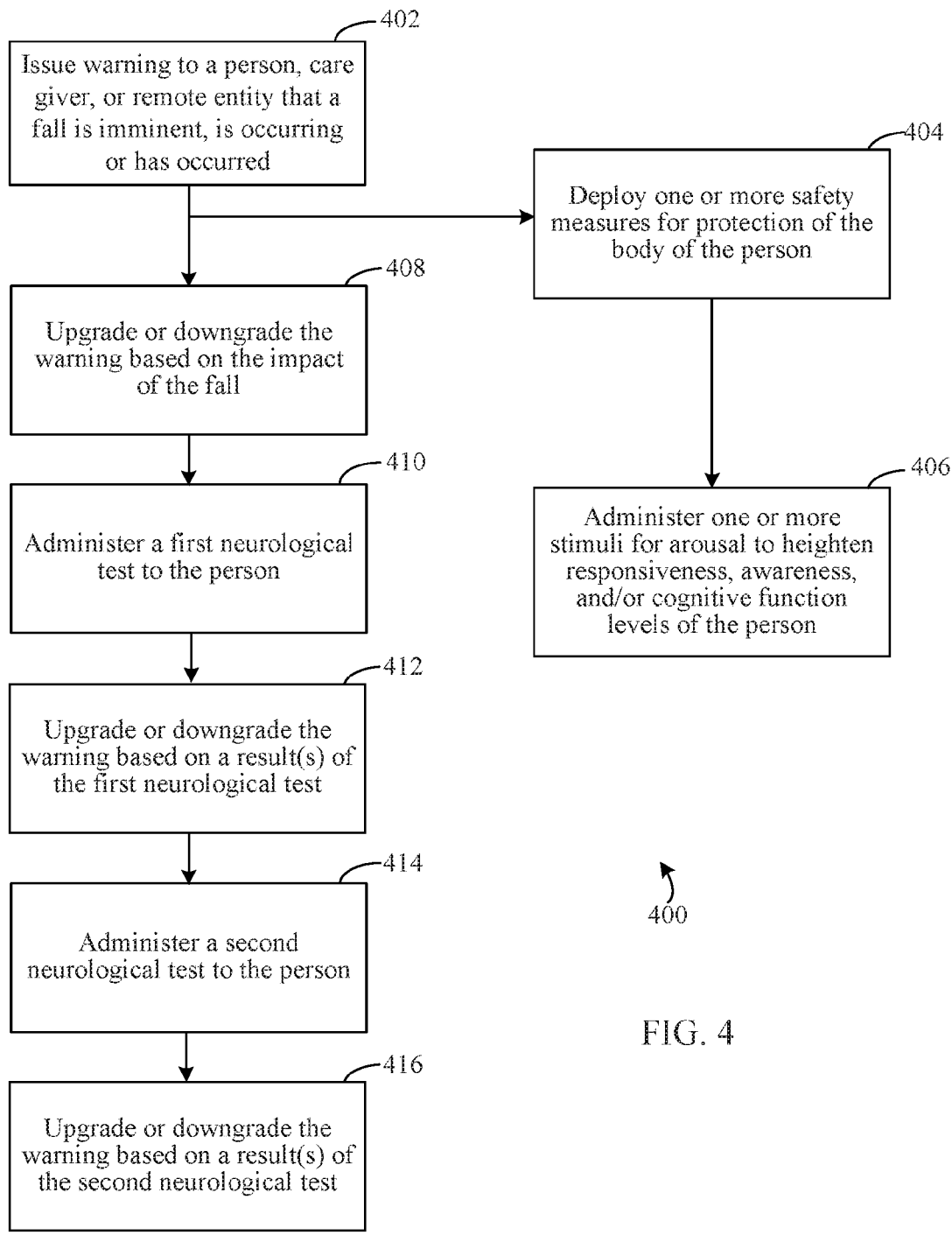
FIG. 4 is a flowchart providing example steps for performing fall detection and taking subsequent remedial action, according to an exemplary embodiment.

For example, FIG. 4 shows a flowchart 400 depicting example steps for providing warnings, safety measures/mitigations, and neurological testing after a fall of a person is detected and/or verified. Fall detector 200 of FIG. 2 and computer 900 of FIG. 9 (described below) may each operate according to flowchart 400, in embodiments. Flowchart 400 may be a further embodiment of steps 308 and 310 of flowchart 300. Other structural and operational embodiments will be apparent to persons skilled in the relevant art(s) based on the discussion regarding flowchart 400. Flowchart 400 is described as follows.

Flowchart 400 may begin with step 402. In step 402, a warning may be issued to the person, a care giver, and/or a remote entity that a fall is imminent, is occurring or has occurred. For example, fall detection unit 204 of FIG. 2 may issue the warning. The warning may be based upon data received from sensor unit 202, body data/signal input unit 206, and/or other components of fall detector 200 shown in FIG. 2. From step 402, flowchart 400 may continue to steps 404 and/or 408.

In step 404, one or more safety measures for protection of the body of the person may be deployed. For example, safety measures as described herein may be deployed to protect the head, neck, chest/torso, lower back, hips, knees, etc. of the person. In embodiments, fall detection unit 204 may issue a signal or a command to activate deployment of the safety measures. The deployment of safety measures may be based in part on an analysis of motion data as described above in flowchart 300 and elsewhere herein, and/or body data or body signals. From step 404, flowchart 400 may continue to step 406.

In step 406, one or more stimuli may be administered to the person to arouse heightened responsiveness, awareness, and/or cognitive function levels. In embodiments, neurological unit 210 may cause stimuli such visual, audio, haptic, electrical, thermal and/or noxious stimuli to be administered to the person.

Step 408 continues from step 402. In step 408, the warning of step 402 may be upgraded or downgraded based on a value of the force of impact of the fall. For example, fall detection unit 204 may cause the warning to be upgraded or downgraded based upon data received from sensor unit 202, such as from accelerometer 218 and/or force detector 222. In embodiments, falls for which the value of the force of impact is above a threshold value may have upgraded warnings as described herein, whereas falls for which the value of the force of impact is below a threshold value may have downgraded warnings as described herein.

In step 410, a first neurological test may be administered to the person. In embodiments, the first neurological test may be any of those described herein, and may require the person to manually or orally input a level of responsiveness or awareness.

In step 412, the warning may be upgraded or downgraded based upon one or more results of the administered first neurological test. In embodiments, test results (e.g., score(s) or other quantitative measures of performance) which are above a threshold value or are determined to be normal may have downgraded warnings as described herein, whereas test results which are below a threshold value or determined to be abnormal may have upgraded warnings as described herein.

In step 414, a second neurological test may be administered to the person. In embodiments, the second neurological test may be any of those described herein, and may require the person to manually or orally input a level of responsiveness, a level of awareness, and/or a level of cognitive function.

In step 416, the warning may be upgraded or downgraded based upon one or more results of the administered second neurological test. In embodiments, test results (e.g., score(s) or other quantitative measures of performance) which are above a threshold value or are determined to be normal may have downgraded warnings as described herein, whereas test results which are below a threshold value or determined to be abnormal may have upgraded warnings as described herein.

In some example embodiments, one or more steps 402, 404, 406, 408, 410, 412, 414, and/or 416 of flowchart 400 may not be performed. Moreover, steps in addition to or in lieu of steps 402, 404, 406, 408, 410, 412, 414, and/or 416 may be performed. Further, in some example embodiments, one or more of steps 402, 404, 406, 408, 410, 412, 414, and/or 416 may be performed out of order, in an alternate sequence, or partially (or completely) concurrently with other steps. For example, it should be noted that the branch from step 402 to steps 404 and/or 408 may be taken substantially concurrently, serially, in a manner that is partially overlapping, or in any other order.

Figure 5:
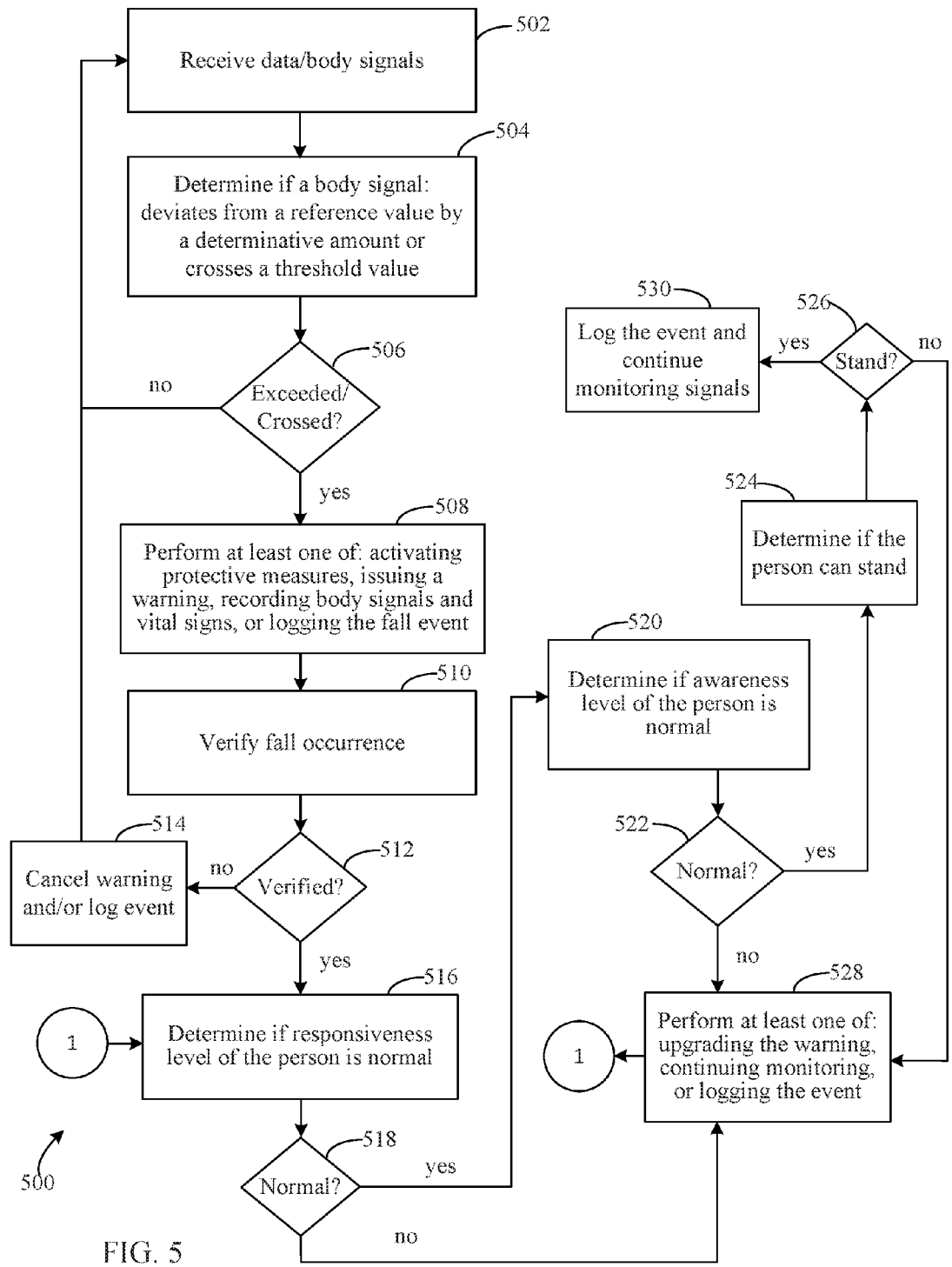
FIG. 5 is a flowchart providing example steps for performing fall detection using body data and body signals, according to an exemplary embodiment.

Fall detection may also be based upon body data and/or body signals. FIG. 5 shows a flowchart 500 providing example steps for performing fall detection using body data and body signals. In the context of FIG. 5, fall detection encompasses detecting imminent falls, falls that occurring, and falls that have occurred. Fall detector 200 of FIG. 2 and computer 900 of FIG. 9 (described below) may each operate according to flowchart 500, in embodiments. Flowchart 500 may be a further embodiment of flowchart 300. Other structural and operational embodiments will be apparent to persons skilled in the relevant art(s) based on the discussion regarding flowchart 500. Flowchart 500 is described as follows.

Flowchart 500 may begin with step 502. In step 502, body data and/or body signals may be received. For example, data related to body state, vital signs, electrical body signals and/or the like may be received at body data/signal input unit 206 of fall detector 200 shown in FIG. 2. In some embodiments, the received data may be received at fall detection unit 204 via body data/signal input unit 206 using communication link 216.

In step 504, it may be determined if a body signal deviates from a reference value by a determinative amount or crosses (or reaches) a threshold value. Such a determination may be performed by fall detection unit 204 in accordance with embodiments described herein.

In step 506, if a deviation exceeds the determinative amount or if a threshold is reached/crossed, flowchart 500 continues to step 508. If not, flowchart 500 returns to step 502.

In step 508, at least one of activating protective measures, issuing a warning, recording body signals and vital signs, or logging the fall event may be performed. For example, fall detection unit 204 may activate or deploy protective measures and/or issue a warning as described above in Sections 5.A and 5.B. Additionally, logging unit 212 may record body signals and/or vital signs and may log the event in accordance with described embodiments.

In step 510, the fall occurrence may be verified. For instance, fall detection unit 204 may verify that fall will occur, is occurring, or has occurred. The verification of the fall occurrence may be based on one or more of body data or body signals as described in this disclosure, e.g., with respect to fall detection algorithms, flowchart 700 of FIG. 7, FIG. 8, example fall factors of Section 4.A and/or fall detections performed by fall detection unit 204 of FIG. 2.

In step 512, if the fall occurrence is verified, flowchart 500 continues to step 516. If not, flowchart 500 continues to step 514.

In step 514, issued warnings may be canceled (e.g., by fall detection unit 204) and the fall occurrence event may be logged (e.g., by logging unit 212), according to described embodiments. From step 514, flowchart 500 returns to step 502.

In step 516, it may be determined if a responsiveness level of the person is normal. The responsiveness level may be determined by administering a neurological test (e.g., a responsiveness test) using neurological unit 210 as previously described.

In step 518, if the responsiveness level of the person is normal, flowchart 500 continues to step 520. If not, flowchart 500 continues to step 528.

In step 520, it may be determined if awareness level of the person is normal. In embodiments, the awareness level may include a level of cognitive function. The awareness level may be determined by administering a neurological test (e.g., an awareness or cognitive test) using neurological unit 210 as previously described.

In step 522, if the awareness level of the person is normal, flowchart 500 continues to step 524. If not, flowchart 500 continues to step 528.

In step 524, it may be determined if the person can stand. For example, sensor unit 202 (e.g., via accelerometer 218, clinometer 220 and/or gyroscope 224) may determine if the person is able to stand upright based upon motion data, body posture or incline, and steadiness of the person (i.e., lack of sway).

In step 526, if it was determined that the person was able to stand, flowchart 500 continues to step 530. If not, flowchart 500 continues to step 528.

Step 528 continues from steps 518, 522 and 526, as noted above. In step 528, at least one of upgrading the warning, continuing monitoring, or logging the event is performed. For instance, fall detection unit 204 may upgrade the warning, as previously described, and sensor unit 202, body data/signal input unit 206, and/or user input unit 208 may continue monitoring signals and data. Logging unit 212 may log the fall occurrence event up to the current time, in accordance with the described embodiments. From step 528, flowchart 500 returns to step 516 via flowchart connector 1.

Step 530 continues from step 526. In step 530, logging the event is performed and monitoring of signals is continued. For example, logging unit 212 may log the fall occurrence event up to the current time, in accordance with the described embodiments. Sensor unit 202, body data/signal input unit 206, and/or user input unit 208 may continue monitoring signals and data.

In some example embodiments, one or more steps 502, 504, 506, 508, 510, 512, 514, 516, 518, 520, 522, 524, 526, 528, and/or 530 of flowchart 500 may not be performed. Moreover, steps in addition to or in lieu of steps 502, 504, 506, 508, 510, 512, 514, 516, 518, 520, 522, 524, 526, 528, and/or 530 may be performed. Further, in some example embodiments, one or more of steps 502, 504, 506, 508, 510, 512, 514, 516, 518, 520, 522, 524, 526, 528, and/or 530 may be performed out of order, in an alternate sequence, or partially (or completely) concurrently with other steps.

Figure 6:
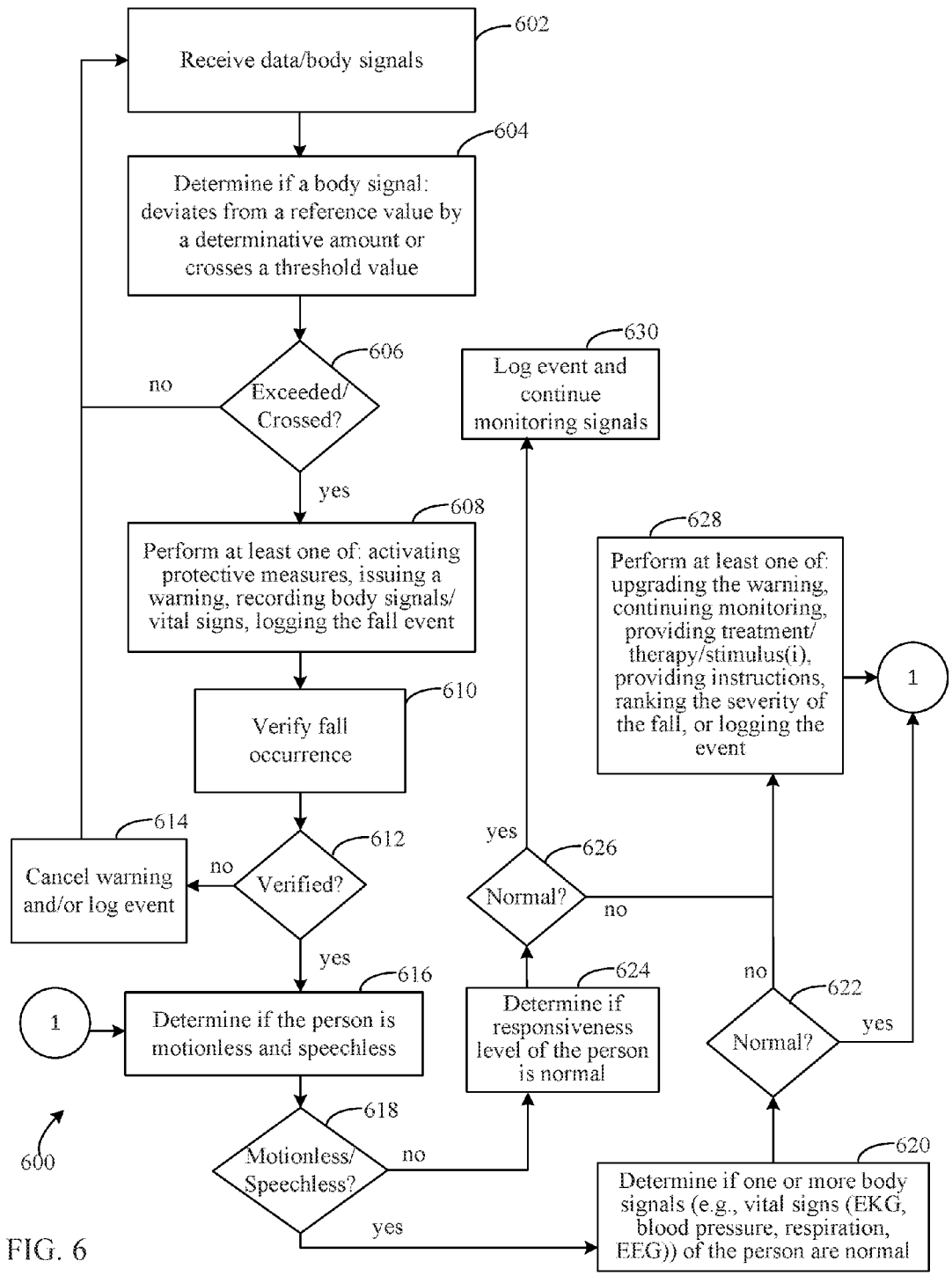
FIG. 6 is a flowchart providing example steps for performing fall detection using body data and body signals, according to an exemplary embodiment.

Turning now to FIG. 6 a flowchart 600 providing example steps for performing fall detection using body data and body signals is shown. In the context of FIG. 6 and flowchart 600, fall detection encompasses detecting imminent falls, falls that are occurring, and falls that have occurred. Fall detector 200 of FIG. 2 and computer 900 of FIG. 9 (described below) may each operate according to flowchart 600, in embodiments. In embodiments, flowchart 600 may be a further embodiment of flowcharts 300 and/or 500. Other structural and operational embodiments will be apparent to persons skilled in the relevant art(s) based on the discussion regarding flowchart 600. Flowchart 600 is described as follows.

Flowchart 600 may begin with step 602. In step 602, body data and/or body signals may be received. For example, data related to body state, vital signs, electrical body signals and/or the like may be received at body data/signal input unit 206 of fall detector 200 shown in FIG. 2. In some embodiments, the received data may be received at fall detection unit 204 via body data/signal input unit 206 using communication link 216.

In step 604, it may be determined if a body signal deviates from a reference value by a determinative amount or crosses (or reaches) a threshold value. Such a determination may be performed by fall detection unit 204 in accordance with embodiments described herein.

In step 606, if a deviation exceeds the determinative amount or if a threshold is reached/crossed, flowchart 600 continues to step 608. If not, flowchart 600 returns to step 602.

In step 608, at least one of activating protective measures, issuing a warning, recording body signals and vital signs, or logging the fall event may be performed. For example, fall detection unit 204 may activate or deploy protective measures and/or issue a warning as described above in Sections 5.A and 5.B. Additionally, logging unit 212 may record body signals and/or vital signs and may log the event in accordance with described embodiments.

In step 610, the fall occurrence may be verified. For instance, fall detection unit 204 may verify that fall will occur, is occurring, or has occurred. The verification of the fall occurrence may be based on one or more of body data or body signals as described in this disclosure, e.g., with respect to fall detection algorithms, flowchart 700 of FIG. 7, FIG. 8, example fall factors of Section 4.A and/or fall detection performed by fall detection unit 204 of FIG. 2.

In step 612, if the fall occurrence is verified, flowchart 600 continues to step 616. If not, flowchart 600 continues to step 614.

In step 614, issued warnings may be canceled (e.g., by fall detection unit 204) and the fall occurrence event may be logged (e.g., by logging unit 212), according to described embodiments. From step 614, flowchart 600 returns to step 602.

In step 616, it may be determined if the person is motionless and speechless. Motion or lack thereof may be determined by sensor unit 202. Speech or lack thereof may be determined by user input unit 208 as previously described.

In step 618, if the person is motionless and speechless, flowchart 600 continues to step 620. If not, flowchart 600 continues to step 624.

In step 620, it may be determined if one or more body signals (e.g., vital signs such as EKG, blood pressure, respiration, EEG, and/or the like) of the person are normal. In embodiments, body data/signal input unit 206 may receive body signals indicative of vital signs and determine if the vital signs are normal based upon one or more comparisons to baseline values and/or threshold values described in embodiments herein.

In step 622, if the vital signs of the person are normal, flowchart 600 returns to step 616 via flowchart connector 1. If not, flowchart 600 continues to step 628.

In step 624, it may be determined if a responsiveness level of the person is normal. The responsiveness level may be determined by administering a neurological test (e.g., a responsiveness test) using neurological unit 210 as previously described.

In step 626, if the responsiveness level of the person is normal, flowchart 600 continues to step 630. If not, flowchart 600 continues to step 628.

Step 628 continues from steps 622 and 626, as noted above. In step 628, at least one of upgrading the warning, continuing monitoring, providing treatment(s), therapy(ies), and/or stimulus(i), providing instructions, ranking the severity of the fall, or logging the event is performed. For instance, fall detection unit 204 may upgrade the warning and/or provide one or more treatments, therapies, and/or stimuli, as previously described in Sections 5.A and 5.B. Fall detection unit 204 may also rank the severity of the fall in accordance with described embodiments herein. In embodiments, one or more of fall detection unit 204, user input unit 208, and communication unit 214 may provide instructions to the person, as described in Section 5.B above. Sensor unit 202, body data/signal input unit 206, and/or user input unit 208 may continue monitoring signals and data. Logging unit 212 may log the fall occurrence event up to the current time, in accordance with the described embodiments. From step 628, flowchart 600 returns to step 616 via flowchart connector 1.

Step 630 continues from step 626. In step 630, logging the event is performed and monitoring of signals is continued. For example, logging unit 212 may log the fall occurrence event up to the current time, in accordance with the described embodiments. Sensor unit 202, body data/signal input unit 206, and/or user input unit 208 may continue monitoring signals and data.

In some example embodiments, one or more steps 602, 604, 606, 608, 610, 612, 614, 616, 618, 620, 622, 624, 626, 628, and/or 630 of flowchart 600 may not be performed. Moreover, steps in addition to or in lieu of steps 602, 604, 606, 608, 610, 612, 614, 616, 618, 620, 622, 624, 626, 628, and/or 630 may be performed. Further, in some example embodiments, one or more of steps 602, 604, 606, 608, 610, 612, 614, 616, 618, 620, 622, 624, 626, 628, and/or 630 may be performed out of order, in an alternate sequence, or partially (or completely) concurrently with other steps.

Operational embodiments describing an exemplary fall detection algorithm are discussed next.

Algorithms for fall detection may be configured and performed in various ways according to embodiments. For example, single and multi-stage detection algorithms are contemplated for embodiments described herein. In one exemplary embodiment as shown in FIG. 7, a flowchart 700 provides example steps of a fall detection algorithm that uses motion-related sensor data and body signals to detect and confirm that a fall is imminent, that a fall is occurring, and/or that a fall has occurred. Flowchart 700 may be a further embodiment of step 306 of flowchart 300, steps 504, 506, 510, and 512 of flowchart 500, and/or steps 604, 606, 610, and 612 of flowchart 600. Other structural and operational embodiments will be apparent to persons skilled in the relevant art(s) based on the discussion regarding flowchart 700. Flowchart 700 is described as follows.

Flowchart 700 may begin with step 702. In step 702, it is determined if a sensor data value threshold is reached or crossed. For example, sensor data such as accelerometer data, clinometer data, gyroscope data, force transducer data, body data and body signal values, and/or the like as described herein, may be received and/or analyzed. In embodiments the sensor data is analyzed by fall detection unit 204 of FIG. 2. The sensor data values are compared to one or more thresholds (i.e., sensor data value thresholds) as will be described in further detail below with respect to FIG. 8. Based on this comparison, a determination of whether a threshold has been reached and/or crossed in an upward direction (a sensor data value exceeds the threshold) or has been reached and/or crossed in a downward direction (a sensor data value falls below the threshold) is made.

In step 704, if it is determined that a sensor data value threshold has not been reached and/or crossed, flowchart 700 continues to step 706. If it is determined that a sensor data value threshold has been reached and/or crossed, flowchart 700 continues to step 708.

In step 706 data associated with the unverified fall event and/or body data/signals are logged. In embodiments, logging unit 212 of FIG. 2 logs the fall event data, body data, and/or and body signals. For example, the log may be written to a memory or storage device as described herein. The log may be used to generate and/or supplement a fall history for a person, and may be used to determine fall detection algorithm performance and efficacy.

In step 708, it is determined if an EMG data value, an clinometer output and/or a gyroscopic output are indicative of a fall. Such indicia, when used, for example, in conjunction with sensor data, increases accuracy in fall detection. In embodiments indicia are determined by fall detection unit 204 of FIG. 2. For instance, EMG data indicating increased or decreased muscle tone (as described herein) of certain muscles and muscle groups may be an indication that fall is imminent, is occurring, or has occurred. Likewise, an clinometer output showing a deviation from an upright body posture may be an indication that fall is imminent, is occurring, or has occurred. Furthermore, gyroscopic outputs that show, for example, sway and/or loss of balance may be an indication that fall is imminent, is occurring, or has occurred. In embodiments, the above-described indicia may be determined by a data value or an output reaching/crossing a threshold or by a data value or an output that deviates from a baseline or normal value by a predetermined amount.

In step 710, if it is determined that a fall indication is not present, flowchart 700 continues to step 712. If it is determined that a fall indication is present, flowchart 700 continues to step 714.

In step 712, the current fall detection is canceled, along with any issued warnings, and flowchart 700 continues to step 706 as described above.

In step 714, the fall detection is confirmed/verified. That is, based upon a threshold being reached and one or more other indicia of the fall, the fall is confirmed/verified. In embodiments, the confirmation/verification is performed by fall detection unit 204 of FIG. 2. When a fall event is confirmed/verified, the positive detection of the fall may be logged (not shown) in logging unit 212 and used to determine the performance and/or efficacy of the fall detection algorithm.

In some example embodiments, one or more steps 702, 704, 706, 708, 710, 712, and/or 714 of flowchart 700 may not be performed. Moreover, steps in addition to or in lieu of steps 702, 704, 706, 708, 710, 712, and/or 714 may be performed. Further, in some example embodiments, one or more of steps 702, 704, 706, 708, 710, 712, and/or 714 may be performed out of order, in an alternate sequence, or partially (or completely) concurrently with other steps.

Figure 8:
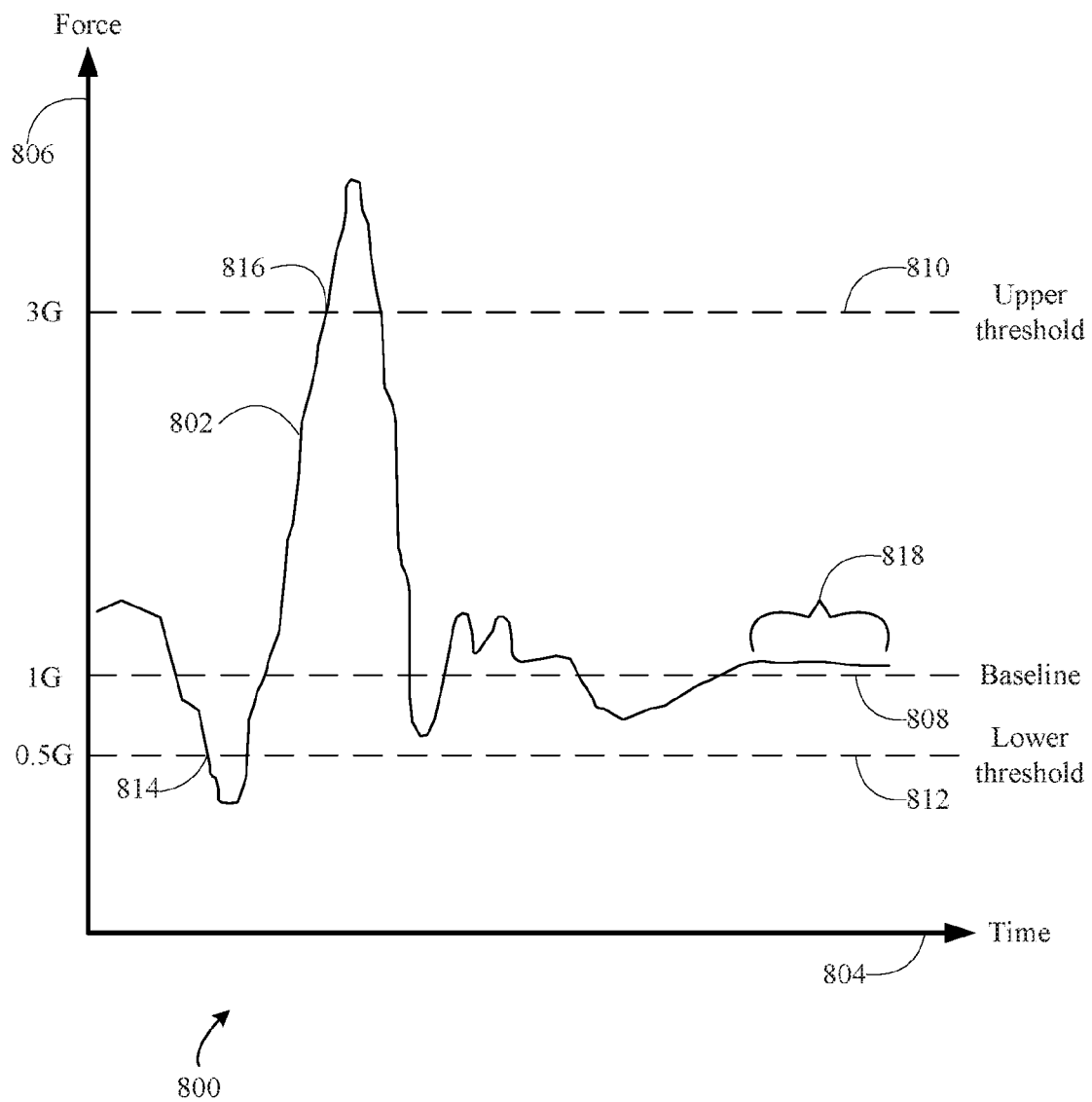
FIG. 8 is a multiphasic graphical representation of changes in a sensor data value over time with respect to value thresholds, according to an exemplary embodiment.

FIG. 8 shows an exemplary, multiphasic graphical representation 800 of a sensor data value 802 with respect to time, according to embodiments. Graphical representation 800 is illustrative of threshold crossings described above with respect to flowchart 700 of FIG. 7.

Graphical representation 800 is depicted with respect to a time axis 804 and a force axis 806. That is, the force of sensor data value 802 varies with respect to time. In the described embodiment, sensor data value 802 is an output of an accelerometer related to a fall from a standing position to the ground, although it is contemplated that any other sensor data value described herein may be represented in a similar fashion with respect to one or more parameters (e.g., the angle of deviation and the rate of deviation of a clinometer output with respect to time, the force of a force transducer/detector output with respect to time, the amount of sway indicated by a gyroscope output with respect to time or with respect to an upright body posture/position, etc.).

Graphical representation 800 includes a baseline force 808, an upper threshold 810 (e.g., a 3G force), and a lower threshold 812 (e.g., a 0.5G force). Graphical representation 800, as shown, may be described as multiphasic in that sensor data value 802 transitions across multiple thresholds (e.g., above upper threshold 810 at an upward crossing 816 and below lower threshold 812 at a downward crossing 814). It is contemplated, however, that in embodiments a single threshold may be used. It should also be noted that the threshold values (3G and 0.5G) are illustrative in nature, and that other threshold values may be used.

In embodiments, a fall detector (e.g., fall detector 200 of FIG. 2) and/or any of its components may perform actions or functions related to a fall event at times corresponding to threshold crossings. For example, detection and verification of the fall, issuance of a warning, and/or deployment of body protection devices may take place as early as sensor data value 802 reached/crossed lower threshold 812 (e.g., a change in force due to a falling motion) and/or before sensor data value 802 reached/crossed upper threshold 810 (e.g., a change in force due to an impact). As previously noted, upper threshold 810 and lower threshold 812 may be set to different values, and in addition, may also be dynamically adapted to increase sensitivity (e.g., to decrease false negative detections), to increase specificity (e.g., to decrease false negative detections such as those that may be caused a person jogging or jumping), and/or to increase speed of detection (e.g., to prevent traumatic injuries) in order to improve performance and/or efficacy of a fall detection algorithm.

For instance, algorithm adaptation (e.g., threshold adaptation) may be based on the overall health state or activities of a person. If a person regularly runs or jogs, accelerometer outputs are typically higher/lower according to the activity motion than when walking or standing still. Thus, thresholds may be adapted to allow for a wider acceleration margin based on activities or on patterns of changes in acceleration regularly or frequently experienced by a person during normal activities. Persons with movement disorders/diseases and/or vision issues may also have adjusted thresholds, but in these instances a person may have thresholds adapted to provide for a more narrow margin of acceleration tolerance.

Additional actions or functions related to a fall event at times corresponding to threshold crossings may also be performed. For example, a warning issued at downward crossing 814 may be upgraded upon approaching, reaching, or crossing upper threshold 810 (e.g., at upward crossing 816). Similarly, warnings may be canceled when sensor data value 802 is maintained (818) at an approximate baseline 808 value for a specified period of time and/or in conjunction with one or more normal value determinations (e.g., a normal level of responsiveness and/or awareness, normal vital signs, etc.).

It should be noted that FIG. 8, as shown, is not drawn to scale.

With respect to the exemplary operational embodiments described above, it should be noted that the steps described in flowcharts 300, 400, 500, 600, 700, and/or 800 may be combined in embodiments. That is, the steps in the preceding flowcharts are not mutually exclusive and may be performed in parallel, substantially in parallel, in an overlapping manner, sequentially, or substantially sequentially in any combination. Additionally, one or more steps of a given flowchart may be added to another flowchart in embodiments, as would be understood by persons of skill in the relevant art(s) having the benefit of this disclosure.

8. Example Computer Embodiments

Fall detector 200, sensor unit 202, fall detection unit 204, body data/signal input unit 206, user input unit 208, neurological unit 210, logging unit 212, a communication unit 214, communication link 216, accelerometer 218, clinometer 220, force detector 222, gyroscope 224, flowcharts 300, 400, 500, 600, 700, and/or any further systems, sub-systems, and/or components disclosed herein may be implemented in hardware (e.g., hardware logic/electrical circuitry), or any combination of hardware with software (computer program code configured to be executed in one or more processors or processing devices) and/or firmware.

Figure 9:
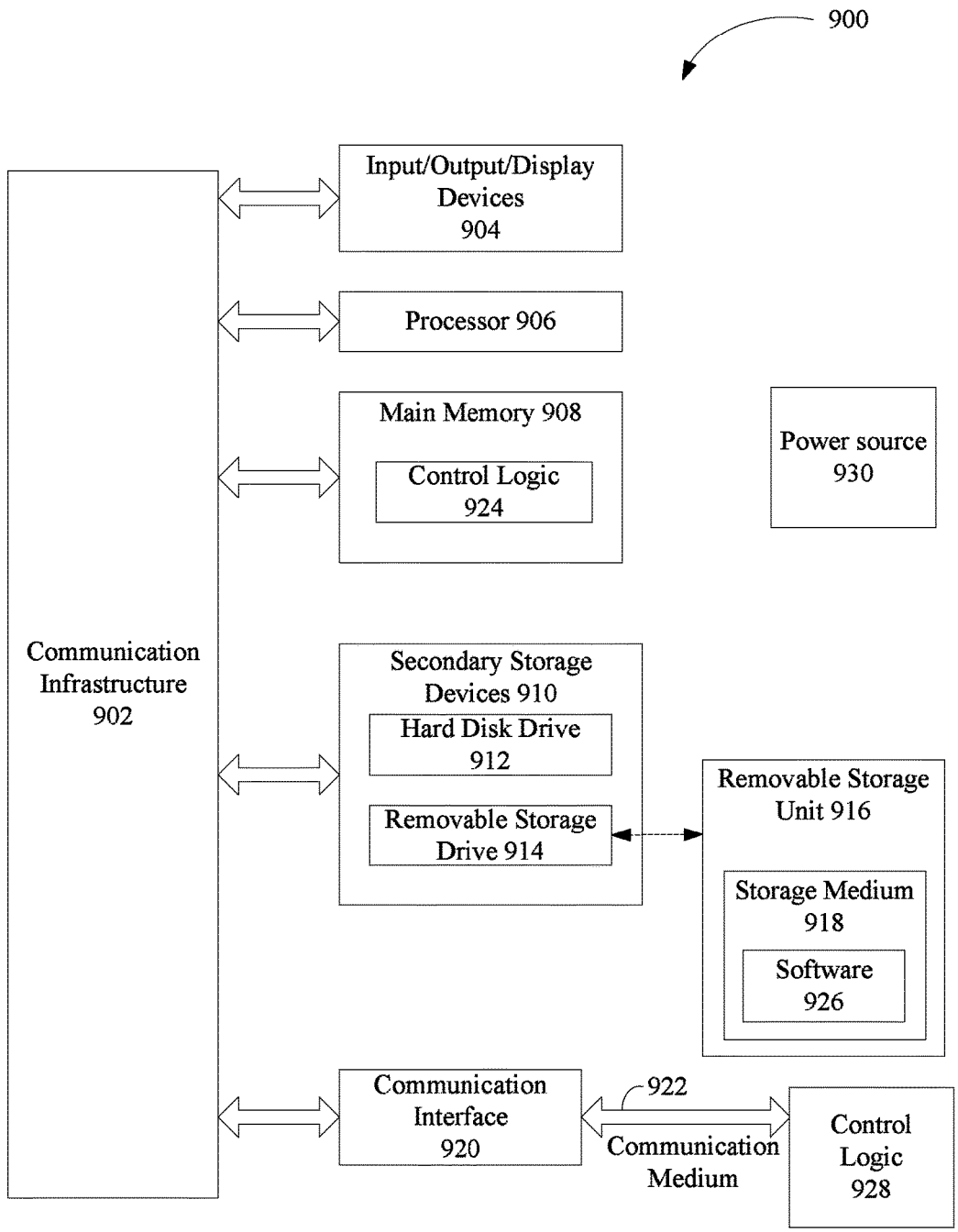
FIG. 9 is a block diagram of a computer system, according to an exemplary embodiment.

The embodiments described herein, including systems, methods/processes, and/or apparatuses/devices, may be implemented using well known processing devices, telephones (e.g., smart phones), processor-based devices, and/or, computers, such as a computer 900 shown in FIG. 9. It should be noted that computer 900 may represent communication devices, processor-based devices, and/or traditional computers in one or more embodiments. For example, fall detector 200 and any of the sub-systems or components respectively contained therein may be implemented using one or more computers 900.

Computer 900 can be any custom made computing device or any commercially available and well known communication device, processing device, and/or computer capable of performing the functions described herein, such as devices/computers available from International Business Machines®, Apple®, Sun®, HP®, Dell®, Cray®, Samsung®, Nokia®, etc. Computer 900 may be any type of computing device.

Computer 900 includes one or more processors (also called central processing units, or CPUs), such as a processor 906. Processor 906 is connected to a communication infrastructure 902, such as a communication bus. In some embodiments, processor 906 can simultaneously operate multiple computing threads.

Computer 900 also includes a primary or main memory 908, such as random access memory (RAM). Main memory 908 has stored therein control logic 924 (computer software), and data.

Computer 900 also includes one or more secondary storage devices 910. Secondary storage devices 910 include, for example, a hard disk drive 912 and/or a removable storage device or drive 914, as well as other types of storage devices, such as memory cards and memory sticks. For instance, computer 900 may include an industry standard interface, such a universal serial bus (USB) interface for interfacing with devices such as a memory stick. Removable storage drive 914 represents a floppy disk drive, a magnetic tape drive, a compact disk drive, an optical storage device, tape backup, etc.

Removable storage drive 914 interacts with a removable storage unit 916. Removable storage unit 916 includes a computer useable or readable storage medium 918 having stored therein computer software 926 (control logic) and/or data. Removable storage unit 916 represents a floppy disk, magnetic tape, compact disk, DVD, optical storage disk, or any other computer data storage device. Removable storage drive 914 reads from and/or writes to removable storage unit 916 in a well-known manner.

Computer 900 also includes input/output/display devices 904, such as touchscreens, LED and LCD displays, monitors, buttons, keyboards, pointing devices, microphones, other audio or vibrational sensors, speakers, etc.

Computer 900 further includes a communication or network interface 918. Communication interface 920 enables computer 900 to communicate with remote devices. For example, communication interface 920 allows computer 900 to communicate over communication networks or mediums 922 (representing a form of a computer useable or readable medium), such as LANs, WANs, the Internet, etc. Network interface 920 may interface with remote sites or networks via wired or wireless connections.

Control logic 928 may be transmitted to and from computer 900 via communication medium 922.

Computer 900 further includes a power source 930 configured to provide power to one or more of the components of computer 900. Power source 930 may be a battery (rechargeable or non-rechargeable), an A/C and/or D/C power source, an electromagnetically chargeable power source, and/or the like.

In embodiments, computer 900 may include any or all of the components described in this section and/or in the Example Fall Detector section described above.

Any apparatus or manufacture comprising a computer useable or readable medium having control logic (software) stored therein is referred to herein as a computer program product or program storage device. This includes, but is not limited to, computer 900, main memory 908, secondary storage devices 910, and removable storage unit 916. Such computer program products, having control logic stored therein that, when executed by one or more data processing devices, cause such data processing devices to operate as described herein, represent embodiments of the invention.

Devices in which embodiments may be implemented may include storage, such as storage drives, memory devices, and further types of computer-readable media. Examples of such computer-readable storage media include a hard disk, a removable magnetic disk, a removable optical disk, flash memory cards, digital video disks, random access memories (RAMs), read only memories (ROM), and the like. As used herein, the terms "computer program medium" and "computer-readable medium" are used to generally refer to the hard disk associated with a hard disk drive, a removable magnetic disk, a removable optical disk (e.g., CDROMs, DVDs, etc.), zip disks, tapes, magnetic storage devices, MEMS (micro-electromechanical systems) storage, nanotechnology-based storage devices, as well as other media such as flash memory cards, digital video discs, RAM devices, ROM devices, and the like. Such computer-readable storage media may store program modules that include computer program logic to implement, for example, fall detector 200, sensor unit 202, fall detection unit 204, body data/signal input unit 206, user input unit 208, neurological unit 210, logging unit 212, a communication unit 214, communication link 216, accelerometer 218, clinometer 220, force detector 222, flowcharts 300, 400, 500, 600, and 700, and/or any further systems, sub-systems, and/or components, as well as any other embodiments disclosed herein. Embodiments of the invention are directed to computer program products comprising such logic (e.g., in the form of program code, instructions, or software) stored on any computer useable medium. Such program code, when executed in one or more processors, causes a device to operate as described herein.

Note that such computer-readable storage media are distinguished from and non-overlapping with communication media (do not include communication media). Communication media typically embodies computer-readable instructions, data structures, program modules or other data in a modulated data signal such as a carrier wave. The term "modulated data signal" means a signal that has one or more of its characteristics set or changed in such a manner as to encode information in the signal. By way of example, and not limitation, communication media includes wireless media such as acoustic, RF, infrared and other wireless media. Embodiments are also directed to such communication media.

9. Conclusion

While various embodiments have been described above, it should be understood that they have been presented by way of example only, and not limitation. It will be apparent to persons skilled in the relevant art that various changes in form and detail can be made therein without departing from the spirit and scope of the embodiments. Thus, the breadth and scope of the embodiments should not be limited by any of the above-described exemplary embodiments, but should be defined only in accordance with the following claims and their equivalents.

What is claimed is:

1. A fall detection system, comprising:
   at least one sensor associated with a user;
   a body data signal unit coupled to the user and configured to receive electromyogram (EMG) data;
   a fall detection unit coupled to the at least one sensor, and configured to filter and analyze a measure of force determined by the at least one sensor and determine at least one of the user falling, the user has fallen, or a fall of the user is imminent based on at least EMG data measured by the body data signal unit from a force of contraction on at least one anti-gravitatory muscle or at least one antagonist of the at least one anti-gravitatory muscle, wherein the EMG data deviates above a first threshold indicating abnormally high muscle tone or below a second threshold indicating abnormally decreased muscle tone;
   a neurological unit coupled to the fall detection unit and configured to administer a neurological test to the user in response to the at least one of the user falling, the user having fallen, or a fall of the user being imminent;
   a user-input unit coupled to the neurological unit and configured to receive a neurological test input from the user; and
   a communication unit coupled to the fall detection unit and to the neurological unit, and configured to communicate with at least one of a care-giver station, an emergency medical technology station, or a remote entity.

2. The fall detection system of claim 1, wherein the at least one sensor is at least one of a tri-axial accelerometer or a force transducer.

3. The fall detection system of claim 1, further comprising a logging unit configured to log a date, a time, an amount of time spent in an unresponsive state, an amount of time spent lying on the ground, and/or the measured force associated with a detected fall.

4. The fall detection system of claim 1, wherein the user-input unit comprises:
   a communication interface configured to solicit the user to reply to the neurological test; and
   at least one of:
      a touch sensitive interface configured to receive the neurological test input from the user, or
      a sound sensitive interface configured to receive the neurological test input from the user.

5. The fall detection system of claim 1, wherein the sensor is at least one of a tri-axial accelerometer, a clinometer, a force transducer, a gyroscope, a body signal sensor, an optical sensor, a motor sensor or a sound sensor; and
   wherein the measure of force comprises at least one of: a change in acceleration along at least one axis of the tri-axial accelerometer; a change in incline or decline detected by the clinometer; a force detected by the force transducer; a sway or a loss of balance detected by the gyroscope, the clinometer, or the tri-axial accelerometer; a body signal detected by the body signal sensor; a body movement detected by the optical sensor; a muscle state detected by the motor sensor; or a sound associated with the user detected by the sound sensor.

6. The fall detection system of claim 1, wherein the neurological unit is configured to administer one or more additional neurological tests,
   wherein the neurological test is a responsiveness test,
   wherein the one or more additional neurological tests are at least one of an awareness test or a cognitive level test, and
   wherein the one or more additional neurological tests are administered in response to an input indicating the user did not fail the responsiveness test.

7. The fall detection system of claim 6, wherein the neurological unit is configured to re-administer the one or more additional neurological tests to the user based on at least one of motor activity of the user, one or more sounds associated with the user, or a time interval.

8. The fall detection system of claim 1, wherein the neurological unit is configured to categorize possible causes of the fall based on three or more of: a type of fall; a presence or absence of breaking arm movements; a body part that first makes contact with a surface; a body position before the fall; a body position during the fall; a direction of the fall; a body position immediately after the fall; a type of kinetic activity before the fall; an amount of time elapsed since the last kinetic activity of the user, a type of kinetic activity; a level of kinetic activity; autonomic activity before, during or after the fall; or neurologic activity before, during or after the fall.

9. A fall detection system, comprising:
   at least one of a tri-axial accelerometer, a clinometer, a force transducer, or a gyroscope attached to a user;
   a fall detection unit coupled to the at least one of the tri-axial accelerometer, the clinometer, the force transducer, or the gyroscope, and configured to filter and analyze motion data or force data received from the at least one of the tri-axial accelerometer, the clinometer, the force transducer, or the gyroscope and determine if the user is falling or that a fall is imminent;
   a neurological unit coupled to the fall detection unit and configured to administer a responsiveness test to the user, wherein the neurological unit is configured to administer, in response to an input indicating the user did not fail the responsiveness test, at least one of an awareness test or a cognitive level test; and
   a user-input unit coupled to the neurological unit and configured a receive a responsiveness test input from the user.

10. The fall detection system of claim 9, further comprising:
    one or more shock absorbing devices placed on at least one of the head, neck, chest, or one or more knees of the user, wherein the one or more shock absorbing devices are configured to be automatically deployed based on a signal or command from the fall detection unit in response to determining that the user is falling or that a fall is imminent.

11. The fall detection system of claim 9, further comprising a body data signal unit configured to receive electromyogram (EMG) data and transmit the EMG data to the fall detection unit; and
    wherein the fall detection unit is configured to verify a fall is occurring based on:
       at least one of the motion data or the force data received from at least one of the tri-axial accelerometer, the clinometer, or the force transducer, and at least one of the EMG data or the motion data received from at least one of the clinometer or the gyroscope.

12. The fall detection system of claim 9, wherein the responsiveness test comprises at least one of:
an orientation test,
a motor test, or
a memory test.

13. The fall detection system of claim 9, wherein the determination by the fall detection unit that the user is falling or that a fall is imminent is based on at least a decrease in autonomic signals below a first autonomic baseline or increase above a second autonomic baseline.

14. The fall detection system of claim 9, wherein the fall detection unit is further configured to rank a severity of the fall based on at least one of a result of the responsiveness test, motion data, a presence of pain, a severity of pain, a force of impact, a site of impact on the body of the user, or a distance traveled by the body of the user after a first impact;
wherein the motion data comprises a duration of time spent falling, a duration of time spent lying down after the fall, or one or more changes in acceleration during the fall.

15. The fall detection system of claim 14, further comprising:
a communication unit coupled to the fall detection unit and to the neurological unit, the communication unit being configured to automatically report at least one of a location of the user or the ranking of the severity of the fall to a remote entity after detecting the fall.

16. The fall detection system of claim 9, wherein the fall detection unit is further configured to sense a force of impact on a part of the body of the user resulting from the fall.

17. A fall detection system, comprising:
at least one sensor associated with a user;
a fall detection unit coupled to the at least one sensor, and configured to filter and analyze a measure of force determined by the at least one sensor and determine at least one of the user falling, the user has fallen, or a fall of the user is imminent;
a neurological unit coupled to the fall detection unit and configured to administer a neurological test to the user in response to the at least one of the user falling, the user having fallen, or a fall of the user being imminent, the neurological test being a responsiveness test, wherein the neurological unit is further configured to administer one or more additional neurological tests to the user in response to an input indicating the user did not fail the responsiveness test, the one or more additional neurological tests being at least one of an awareness test or a cognitive level test;

a user-input unit coupled to the neurological unit and configured to receive a neurological test input from the user; and a communication unit coupled to the fall detection unit and to the neurological unit, and configured to communicate with at least one of a care-giver station, an emergency medical technology station, or a remote entity.

18. The fall detection system of claim 17, wherein the neurological unit is configured to re-administer the one or more additional neurological tests to the user based on at least one of motor activity of the user, one or more sounds associated with the user, or a time interval.

19. The fall detection system of claim 17, further comprising:
a body data signal unit coupled to the user and configured to receive electromyogram (EMG) data and transmit the EMG data to the fall detection unit, wherein the determination by the fall detection unit that the user is falling, the user has fallen, or that a fall of the user is imminent is further based on at least EMG data measured by the body data signal unit from at least one anti-gravitatory muscle where the EMG data deviates above a first threshold indicating abnormally high muscle tone or below a second threshold indicating abnormally decreased muscle tone.

20. The fall detection system of claim 19, wherein the determination by the fall detection unit that the user is falling, the user has fallen, or that a fall of the user is imminent is further based on a force of contraction on at least one anti-gravitatory muscle or at least one antagonist of the at least one anti-gravitatory muscle.

* * * * *